US012702716B2

(12) United States Patent
Hsieh et al.

(10) Patent No.: US 12,702,716 B2
(45) **Date of Patent: *Aug. 11, 2026**

(54) MONOCYTE-SPECIFIC APTAMERS AND USES THEREOF FOR DELIVERING THERAPEUTIC AGENTS TO HEART

(71) Applicant: Academia Sinica, Taipei (TW)

(72) Inventors: Patrick Ch Hsieh, Taipei (TW); Hsien-Ming Lee, Taipei (TW); Keng-Jung Lee, New Taipei City (TW); Hung-Chih Chen, Changhua County (TW)

(73) Assignee: Academia Sinica, Taipei (TW)

(*) Notice: Subject to any disclaimer, the term of this patent is extended or adjusted under 35 U.S.C. 154(b) by 778 days.

This patent is subject to a terminal disclaimer.

(21) Appl. No.: 17/927,743

(22) PCT Filed: May 26, 2021

(86) PCT No.: PCT/US2021/034370

§ 371 (c)(1),
(2) Date: Nov. 25, 2022

(87) PCT Pub. No.: WO2021/242934

PCT Pub. Date: Dec. 2, 2021

(65) Prior Publication Data

US 2023/0201359 A1 Jun. 29, 2023

Related U.S. Application Data

(60) Provisional application No. 63/030,555, filed on May 27, 2020.

(51) Int. Cl.

| | |
|---|---|
| ***C12N 15/115*** | (2010.01) |
| ***A61K 47/54*** | (2017.01) |
| ***A61K 47/60*** | (2017.01) |
| ***A61K 47/69*** | (2017.01) |
| ***A61P 9/10*** | (2006.01) |
| ***C12N 15/10*** | (2006.01) |

(52) U.S. Cl.

CPC ............ *A61K 47/549* (2017.08); *A61K 47/60* (2017.08); *A61K 47/6911* (2017.08); *A61K 47/6929* (2017.08); *A61P 9/10* (2018.01); *C12N 15/1048* (2013.01); *C12N 15/115* (2013.01); *C12N 2310/16* (2013.01)

(58) Field of Classification Search

CPC .......................... C12N 2310/16; C12N 15/115

See application file for complete search history.

(56) References Cited

U.S. PATENT DOCUMENTS

2012/0164214 A1 6/2012 Machluf et al.

FOREIGN PATENT DOCUMENTS

WO WO2016168884 A1 10/2016

OTHER PUBLICATIONS

Yang, Science, 1996, 272: 1343-1347.*
Knappenberger, eLife, 2018, 7: 1-23.*
Dieckmann, J. Mol. Biol., 1997, 273: 467-478.*
Bishop et al., Circ. Res., 2015, 117: 65-79.*
Cheng et al., Adv. Healthcare Mater., 2016, 5: 2686-2697.*
Cheng B et al., Biomimicking platelet-monocyte interactions as a novel targeting strategy for heart healing. Adv Healthc Mat. 2016;5:2686-2697.

* cited by examiner

*Primary Examiner* — Ileana Popa
(74) *Attorney, Agent, or Firm* — Rei-Cheng Jason Hsu

(57) ABSTRACT

Monocyte-specific nucleic acid aptamers and lipid nanoparticles comprising such for use in drug delivery. Also disclosed herein are use of the aptamer-based lipid nanoparticle drug delivery system for treating heart injury.

17 Claims, 11 Drawing Sheets

Specification includes a Sequence Listing.

SEQUENCE LISTING

```
<160> NUMBER OF SEQ ID NOS: 7

<210> SEQ ID NO 1
<211> LENGTH: 40
<212> TYPE: DNA
<213> ORGANISM: Unknown
<220> FEATURE:
<223> OTHER INFORMATION: Core nucleotide sequence of an embodiment of
      the monocyte-targeting aptamer of the present invention

<400> SEQUENCE: 1

ggatgggagg gagggggctc gtggcggcta gggggtataa                          40


<210> SEQ ID NO 2
<211> LENGTH: 80
<212> TYPE: DNA
<213> ORGANISM: Unknown
<220> FEATURE:
<223> OTHER INFORMATION: An embodiment of the monocyte-targeting aptamer
      flanked by primer sites
```

<400> SEQUENCE: 2
acgctcggat gccactacag ggatgggagg gagggggctc gtggcggcta gggggtataa 60
ctcatggacg tgctggtgac 80

<210> SEQ ID NO 3
<211> LENGTH: 20
<212> TYPE: DNA
<213> ORGANISM: Unknown
<220> FEATURE:
<223> OTHER INFORMATION: An embodiment of a 5' primer site for core nucleotide sequence of the aptamer of the present invention

<400> SEQUENCE: 3
acgctcggat gccactacag 20

<210> SEQ ID NO 4
<211> LENGTH: 100
<212> TYPE: DNA
<213> ORGANISM: Unknown
<220> FEATURE:
<223> OTHER INFORMATION: Nucleotide sequence J10 which is an embodiment of the aptamer of the present invention that includes two primers and anchor

<400> SEQUENCE: 4
caatagagtc gtacaggtcg acgctcggat gccactacag ggatgggagg gagggggctc 60
gtggcggcta gggggtataa ctcatggacg tgctggtgac 100

<210> SEQ ID NO 5
<211> LENGTH: 100
<212> TYPE: DNA
<213> ORGANISM: unknown
<220> FEATURE:
<223> OTHER INFORMATION: Scrambled nucleotide sequence S2 used as control in experiments

<400> SEQUENCE: 5
caatagagtc gtacaggtcg tgagaaggcg ttggtctatc ggggtcgtgg actgtccaag 60
ggcatgaccg gtctgacggt ggccagagac gcaggagggg 100

<210> SEQ ID NO 6
<211> LENGTH: 20
<212> TYPE: DNA
<213> ORGANISM: Unknown
<220> FEATURE:
<223> OTHER INFORMATION: An embodiment of a 3' primer site for core nucleotide sequence of the aptamer of the present invention

<400> SEQUENCE: 6
ctcatggacg tgctggtgac 20

<210> SEQ ID NO 7
<211> LENGTH: 20
<212> TYPE: DNA
<213> ORGANISM: Unknown
<220> FEATURE:
<223> OTHER INFORMATION: An embodiment of anchor nucleic acid fragment for the monocyte-targeting aptamer of the present invention

<400> SEQUENCE: 7
caatagagtc gtacaggtcg 20

MONOCYTE-SPECIFIC APTAMERS AND USES THEREOF FOR DELIVERING THERAPEUTIC AGENTS TO HEART

BACKGROUND OF THE INVENTION

Reliance on the circulatory system for the delivery of therapeutics has long been the method of choice for many disease treatments as it is the least arduous method for the patients, compared to more invasive methods such as surgery. It is not practical in many cases however, as diseases with low vascular density or vascular permeability can reduce drug deliverability. Recruitment of immune cells, such as monocytes, takes place as a natural response to a change in the physiological environment. By exploiting the ability of immune cells to penetrate into diseased sites, the drug delivery platform disclosed herein is capable of acting as a vehicle to target drug delivery into the site of disease injury with recruited monocytes without solely relying on the circulatory system.

Reduced blood supply to the heart following an ischemic myocardial injury render drug delivery through the circulatory system to be ineffective and thus, help is needed to achieve better delivery of the drugs to the intended location. Vascular permeability has been utilized as a method of passive drug delivery, however, studies have shown that this phenomenon only occurs transiently in the heart and the time window it provides is therefore not long enough for a meaningful delivery of therapeutics. Cheng et al., *Adv. Healthc. Mater.* 5, 2686-2697 (2016) and Lundy et al., *Sci. Rep.* 6, 25613 (2016). Recruitment of immune cells, such as monocytes, takes place as a natural response to a change in the physiological environment. After a myocardial injury, splenic monocytes are recruited to help heal the myocardium. Nahrendorf et al. *J. Exp. Med.* 204, 3037-3047 (2007) and Swirski et al., *Science* 325, 612-616 (2009). Disclosed herein is a drug delivery platform capable of selectively attaching onto the surface of circulating monocytes in the blood stream that can act as a vehicle to target drug delivery into the site of cardiac injury with recruited monocytes.

SUMMARY OF THE INVENTION

The present disclosure is based, at least in part, on the identification of nucleic acid aptamers having high binding affinity and specificity to monocytes and the development of an aptamer-based lipid nanoparticle drug delivery system. This drug delivery system has been used successfully in delivering a therapeutic agent to injured heart sites for treatment of heart ischemia reperfusion injury.

Accordingly, the present disclosure provides, in some aspects, a monocyte-targeting lipid nanoparticle for delivering a therapeutic or diagnostic agent to a heart site, comprising a lipid nanoparticle, a monocyte-specific nucleic acid aptamer, and an agent for treating or diagnosing a heart injury. The monocyte-specific nucleic acid aptamer is attached to the lipid nanoparticle and the agent is encapsulated by the lipid nanoparticle. Further, the monocyte-specific nucleic acid aptamer comprising a core nucleotide sequence at least 85% identical to 5'-GGA TGG GAG GGA GGG GGC TCG TGG CGG CTA GGG GGT ATA A-3' (SEQ ID NO:1). In some embodiments, the aptamer comprises the core nucleotide sequence of SEQ ID NO:1.

Any of the monocyte-specific nucleic acid aptamers disclosed herein may comprises a 5' primer site and 3' primer site flanking the core nucleotide sequence. For example, the 5' primer site may comprise the nucleotide sequence of 5'-AC GCT CGG ATG CCA CTA CAG-3' (SEQ ID NO: 3), and/or the 3' primer site comprises the nucleotide sequence of 5'-CT CAT GGA CGT GCT GGT GAC-3' (SEQ ID NO: 4). In specific examples, the aptamer may comprises the nucleotide sequence of 5'-AC GCT CGG ATG CCA CTA CAG GGA TGG GAG GGA GGG GGC TCG TGG CGG CTA GGG GGT ATA ACT CAT GGA CGT GCT GGT GAC-3' (SEQ ID NO: 2).

Alternatively or in addition, the monocyte-specific nucleic acid aptamer may further comprise (conjugated to) an anchor nucleic acid fragment. In some examples, the anchor nucleic acid fragment comprises the nucleotide sequence of 5'-CAA TAG AGT CGT ACA GGT CG-3'(SEQ ID NO: 7), which can be located at the 5' end of the aptamer or the 3' end of the aptamer.

In some embodiments, the lipid nanoparticle comprises a conjugate comprising a docking nucleic acid fragment attached to a lipid. The docketing nucleic acid fragment comprises a nucleotide sequence that is complementary to the anchor nucleic acid fragment conjugated to the monocyte-specific nucleic acid aptamer or a portion thereof. As such, the anchor nucleic acid fragment forms base pairs with the docking nucleic acid fragment, thereby immobilizing the monocyte-specific nucleic acid aptamer on the lipid nanoparticle. The docking nucleic acid fragment may be attached to the lipid directly or via a linker, for example, a polyethylene glycol (PEG) linker. In some examples, the lipid is 1,2-Distearoyl-sn-glycero-3-phosphorylethanolamine (DSPE).

In some examples, the therapeutic agent can be an agent for treating a heart injury, for example, an agent for treatment of a heart ischemia reperfusion injury. Such an agent can be an HIF-1α prolyl hydroxylase-2 (PHD2) inhibitor. Examples include, but are not limited to, IOX2, MK-8617, 2-methoxyestradiol, AKB-4924, IOX3 (FG-2216), FG-4497, roxadustat (FG-4592) Vadadustat (AKB-6548), Daprodustat (GSK1278863), Desidustat (ZYAN-1), Molidustat (Bay 85-3934) IOX4, Enarodustat (JTZ-951)), or a combination thereof. In some examples, the diagnostic agent is for diagnosing a heart injury.

Further, provided herein is a pharmaceutical composition, comprising a monocyte-targeting lipid nanoparticle as disclosed and a pharmaceutically acceptable carrier. Such a pharmaceutical composition can be used, for example, for delivering a suitable therapeutic agent or diagnostic agent to an injured heart site. In some examples, the method may comprise administering to a subject in need thereof an effective amount of the pharmaceutical composition, which, in some examples, may comprise a monocyte-specific lipid nanoparticle that comprises a therapeutic agent or diagnostic agent for treating or detecting a heart injury. In some examples, the subject may be a human patient having or at risk for a heart ischemia reperfusion injury.

Also within the scope of the present disclosure are pharmaceutical compositions comprising any of the monocyte-specific lipid nanoparticles disclosed herein for use in delivering a therapeutic agent or diagnostic agent to an injured site (e.g., an injured heart site) and uses of such monocyte-specific lipid nanoparticles for manufacturing a medicament, which can be used for the intended medical purposes as disclosed herein.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to the drawing in combination with the detailed description of specific embodiments presented herein.

FIGS. 1A and 1B: diagrams depicting binding of monocyte specific aptamers to RAW264.7 (murine monocyte cell line) and J774A.1 (murine monocyte cell line), respectively. The nucleic acid aptamers were identified using the SELEX approach after around 20 rounds of selection cycles and amplified with PCR. Top panels are photos showing comparison of binding ability between monocyte and endothelial cell against aptamer. Bottom panels are charts showing the gradual increase of binding activity of the aptamers (conjugated to a fluorescent dye) to the monocyte cells after several rounds sections. FIG. 1C: a chart showing the biding affinity of aptamers (AptR) against RAW264.7. FIG. 1D: a chart showing the binding affinity of aptamers (AptJ) against J774A.1. FIG. 1E: a chart showing in vitro monocyte specific aptamer selection using quantitative PCR. The specificity of each aptamer candidate to mouse monocyte cell lines RAW264.7 and J774A.1 was tested.

FIG. 2A: depicts a graph showing the amount of Cy5-labeled J10 aptamer and Cy5-labeled S2 aptamer in the monocyte cells lines RAW264.7 and J774A.1 and the mouse endothelial cell line SVEC as measured by flow cytometry. Mouse endothelial cell line SVEC was used as a negative selection. The S2 aptamer had the same nucleotide composition as J10 aptamer but randomized the sequence. Two-way ANOVA with a Tukey adjustment was used to analyze the data where $*P<0.05$; $P<0.01$; $*P<0.001$ were significant. FIG. 2B: Top panel depicts images showing the accumulating amount of J10 and S2 aptamers in infarct area of the injured hearts as measured by PCR. Bottom panel depicts quantification of PCR results. Unpaired Student's t-test was used to analyze the data where $*P<0.05$; $P<0.01$; $*P<0.001$ were significant. FIG. 2C: depicts images showing in vivo targeting of S2 aptamer-QD655 (top panel) and J10 aptamer-QD655 (bottom panel) to circulating CX3CR1-GFP$^+$ monocytes via intravital imaging. The aptamer was conjugated with quantum dots QD655. Scale bars shown represent 100 μm. FIG. 2D: depicts a graph showing ex vivo targeting of J10 aptamer against circulating monocytes examined with flow cytometry to analyze the amount of Cy5-J10 associated with CD45+ and CD11b$^+$ cells isolated from peripheral blood. Unpaired Student's t-test was used to analyze the data where $*P<0.05$; $P<0.01$; $*P<0.001$; $****P<0.0001$ were significant.

FIG. 4A: Mass spectrum of the linker for aptamer conjugation. FIG. 4B: Mass spectrum of the Mal-PEG2000-DSPE lipids. FIG. 4C: Mass spectrum of the linker-PEG2000-DSPE lipids.

FIG. 5A: depicts a schematic of the step-wise synthesis of aptamer-conjugated lipid nanoparticles (LNPs) encapsulated with the drug IOX2. FIG. 5B: depicts images of lipid nanoparticles (LNPs), IOX2-loaded LNPs, IOX2-loaded LNPs modified with the S2 aptamer, and IOX2-loaded LNPs modified with the J10 aptamer under a cryo-electron microscope. Arrows indicate the conjugated aptamers and arrow heads indicate precipitation of IOX2. Scale bars shown represent 100 nm. FIG. 5C: depicts an image of high performance liquid chromatography (HPLC) spectra of lipid nanoparticles (LNPs), and IOX2-loaded LNPs prepared at initial drug to lipid ratios of 0.4, 0.2, and 0.1. FIG. 5D: depicts a graph showing in vitro binding affinity analysis of aptamer-IOX2-LNPs labeled with DiD lipophilic cyanine dyes in the mouse monocyte cell lines J774A.1 and RAW264.7 and the mouse endothelial cell line SVEC. Two-way ANOVA with a Tukey adjustment was used to analyze the data where $****P<0.0001$, $*P<0.05$ were significant. FIG. 5E: depict images showing accumulation of DiD-labelled aptamer-IOX2-LNPs in the injured mouse heart. Images collected via IVIS imaging. Scale bars shown represent 100 μm. FIG. 5F: depicts a graph showing the quantitative analysis of DiD-labelled aptamer-IOX2-LNPs in the injured heart using IVIS. One-way ANOVA with a Tukey adjustment was used to analyze the data where $****P<0.0001$, $*P<0.05$ were significant. FIG. 5G: depicts images of aptamer-IOX2-LNPs (top panel: S2-IOX2-LNPs; bottom panel: J10-IOX2-LNPs) in the infarct area under an intravital microscope. The aptamer-LNPs were labelled with the DiD lipophilic cyanine dyes. Scale bars shown represent 100 μm. FIG. 5H: depicts a graph showing biodistribution of aptamer-IOX2 LNPs in organs of a mouse. Two-way ANOVA with a Tukey adjustment was used to analyze the data where $****P<0.0001$, $*P<0.05$ were significant.

FIG. 7A: Images collected via IVIS imaging. Scale bar as shown is 100 μm. FIG. 7B: Quantitative analysis of DiD labelled aptamer-IOX2-LNPs in the injured heart using IVIS. One-way ANOVA with a Tukey adjustment was used to analyze the data where $*P<0.05$; $P<0.01$; $*P<0.001$; $**P<0.0001$ were significant. FIG. 7**C: Recruitment of CCR2-RFP$^+$ cells in the injured heart after IR captured via an intravital microscope. Scale bar as shown is 100 μm.

FIG. 8A: is an image depicting a schematic of an experimental design for in vivo functional evaluation of aptamer-IOX2-LNPs in the mouse cardiac ischemia reperfusion injury model.

LNP treatment as assessed by Western blotting analysis. Top panel is a representative image of Western blot and bottom panel is quantitative analysis of Western blot analysis. FIG. 8D: Images of slides stained for α-smooth muscle actin (α-SMA) and isolectin (ISO) to examine the effects of aptamer-IOX2-LNPs on angiogenesis in the injured mouse heart. FIG. 8E: Graph showing quantifying α-SMA positive vessels in the injured mouse heart after aptamer-IOX2-LNPs treatment. FIG. 8F: Graph showing quantifying ISO positive vessels in the injured mouse heart after aptamer-IOX2-LNPs treatment. FIGS. 8I-8P depict graphs showing the effects of aptamer-IOX2-LNPs on the heart function twenty-one days after IR in a mouse. FIG. 8I: The effects of aptamer-IOX2-LNPs on ejection fraction (EF) twenty-one days after IR. FIG. 8J: The effects of aptamer-IOX2-LNPs on fraction shortening (FS) twenty-one days after IR. FIG. 8K: The effects of aptamer-IOX2-LNPs on end systolic volume (ESV) twenty-one days after IR. FIG. 8L: The effects of aptamer-IOX2-LNPs on end diastolic volume (EDV) twenty-one days after IR. FIG. 8M: The effects of aptamer-IOX2-LNPs on dp/dt maximum (dp/dt max) twenty-one days after IR. FIG. 8N: The effects of aptamer-IOX2-LNPs on dp/dt minimum (dp/dt min) twenty-one days after IR. FIG. 8O: The effects of aptamer-IOX2-LNPs on ESPVR twenty-one days after IR. FIG. 8P: The effects of aptamer-IOX2-LNPs on EDPVR twenty-one days after IR.

FIG. 9A: The effects of aptamer-IOX2-LNPs on aspartate aminotransferase (AST). FIG. 9B: The effects of aptamer-IOX2-LNPs on alanine aminotransferase (ALT). FIG. 9C: The effects of aptamer-IOX2-LNPs on blood urea nitrogen (BUN). FIG. 9D: The effects of aptamer-IOX2-LNPs on creatinine (CREA). FIG. 9E: The effects of aptamer-IOX2-LNPs on alkaline phosphatase (ALP).

DETAILED DESCRIPTION OF THE INVENTION

Figure 1A:
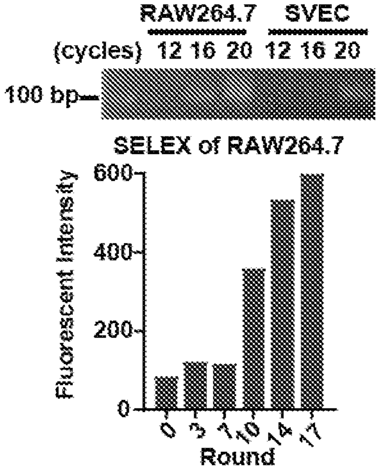
FIGS. 1A-1E include diagrams depicting cell-based systematic evolution of ligands by exponential enrichment (SELEX) selection of aptamers having high binding affinity to monocytes.

The recruitment of macrophages to a disease site is a key event that happens during pathogenesis in patients with acute or chronic diseases. Pawelec et al., *Current Opinion in Immunology.* 2014; 29:23-28. These macrophages first appear as monocytes in blood vessels. Gordon et al., *Nature Reviews Immunology.* 2005; 5:953-964. The circulating monocytes would then travel to the vessel that closest to the disease site, and then reach the site by penetrating through the endothelial lining, a process known as extravasation. Hume, *Current Opinion in Immunology.* 2006; 18:49-53.

The present disclosure is based, at least in part, on the development of nucleic acid aptamers (e.g., J10) that selectively target and bind to monocytes, and the development of an aptamer-based lipid nanoparticle targeting system comprising such monocyte-specific nucleic acid aptamers, such as J10, on surfaces of the lipid nanoparticles. Such aptamer-labeled lipid nanoparticles may serve as an advantageous drug delivery vehicle, which is capable of using the circulating blood cells such as monocytes as a 'shuttle' to allow a therapeutic agent or diagnostic agent encapsulated by the aptamer-labeled lipid nanoparticles to reach a target site of interest, such as an infarct heart area. Once the circulating monocytes that carry the aptamer-labeled lipid nanoparticles cross the endothelial lining, they would be activated to form macrophages. Subsequently, these self-activated macrophages would phagocytize the aptamer-labeled lipid nanoparticles, allowing the encapsulated drugs (e.g., a hypoxic response stimulator such as IOX2) to release or function inside the macrophages, thereby exerting its therapeutic effect.

Accordingly, described herein are monocyte-targeting nucleic acid aptamers, such as J10, aptamer-based lipid nanoparticle monocyte targeting systems, pharmaceutical compositions comprising such, and methods for delivering a therapeutic or diagnostic agent to a target site of interest, such as an infarct heart area, for treating a target disease such as ischemic heart disease (IHD).

Monocyte-Targeting Nucleic Acid Aptamers

Described herein are nucleic acid aptamers that target and bind to monocytes (e.g., J10). A nucleic acid aptamer as used herein refers to a nucleic acid molecule (DNA or RNA) having a binding activity for a particular immune cell (e.g., monocytes). The monocyte-targeting aptamers of the present disclosure, in linear or circular form, may be a RNA, a DNA (e.g., a single-stranded DNA), a modified nucleic acid, or a mixture thereof. The monocyte-targeting aptamers may be non-naturally molecules (e.g., containing a nucleotide sequence not existing in native genes or containing modified nucleotides not existing in nature). Alternatively or in addition, monocyte-targeting aptamers may not contain a nucleotide sequence that encodes a functional peptide.

In some embodiments, the monocyte-targeting aptamer disclosed herein may comprise a core nucleotide sequence at least 70% (e.g., 80%, 85%, 90%, 95%, or 98%) identical to 5'-GGATGGGAGG-GAGGGGGCTCGTGGCGGCTAGGGGGTATAA-3' (SEQ ID NO: 1). In some examples, the monocyte-targeting nucleic acid aptamer disclosed herein may comprise a nucleotide sequence of the core nucleic sequence of SEQ ID NO: 1.

In addition to the core nucleotide sequence disclosed herein, the monocyte-targeting aptamer may further comprise a primer site at the 5' end (5' primer site) of the core sequence, at the 3' end (3' primer site) of the core sequence, or both. In some examples, the monocyte-targeting aptamer disclosed herein may comprise a 5' primer site, which may comprise a nucleotide sequence at least 70% (e.g., 80%, 85%, 90%, 95%, 98%, or 100%) identical to 5'-AC GCT CGG ATG CCA CTA CAG-3' (SEQ ID NO: 3). Alternatively or in addition, the monocyte-targeting aptamer disclosed herein may comprise a 3' primer site, which may comprise a nucleotide sequence at least 70% (e.g., 80%, 85%, 90%, 95%, 98%, or 100%) identical to 5'-CT CAT GGA CGT GCT GGT GAC-3'(SEQ ID NO: 6). In some examples, the monocyte-targeting aptamer disclosed herein may comprise a 5' primer site comprising the nucleotide sequence of 5'-AC GCT CGG ATG CCA CTA CAG-3' (SEQ ID NO: 3), and the 3' primer site comprising the nucleotide sequence of 5'-CT CAT GGA CGT GCT GGT GAC-3' (SEQ ID NO: 6) flanking a core nucleotide sequence comprising the nucleic sequence of SEQ ID NO: 1. In some examples, the monocyte-targeting aptamer disclosed herein may comprise the nucleotide sequence of 5'-ACGCTCGGATGC-CACTACAGGGATGGGAG GGAGGGGGCTCGTGGCGGCTAGGGGGTATAACT-CATGGACGTGCTGGTGAC-3' (SEQ ID NO: 2) or a nucleotide sequence at least 70% (e.g., 80%, 85%, 90%, 95%, or 98%) identical to SEQ ID NO:2.

In some embodiments, the monocyte-targeting aptamer disclosed herein may be conjugated to an anchor nucleic acid fragment, which may facilitate attachment of the aptamer to a lipid nanoparticle. In some examples, an anchor nucleic acid fragment may be conjugated to the 3' end of the monocyte-targeting aptamer disclosed herein. In some examples, an anchor nucleic acid fragment may be conjugated to the 5' end of the monocyte-targeting aptamer disclosed herein. In some examples, the anchor nucleic acid fragment may comprise a nucleotide sequence of 5'-CAATAGAGTCGTACAGGTCG-3' (SEQ ID NO: 7).

In specific examples, a monocyte-targeting aptamer may comprise the nucleotide sequence of 5'-CAATAGAGTCGTACAGGTCGACGCTCGGATGC-CACTACAGGGATGG GAGG-GAGGGGGCTCGTGGCGGCTAGGGGGTATAACT-CATGGACGTGCTGGTGAC-3' (SEQ ID NO: 4), in which the 5' underlined fragment is an anchor nucleic acid fragment, the italicized regions are the 5' and 3' primer sites, and the fragment in boldface is the core nucleotide sequence for monocyte binding.

The "percent identity" of two nucleic acids is determined using the algorithm of Karlin and Altschul *Proc. Natl. Acad. Sci.* USA 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215:403-10, 1990. BLAST nucleotide searches can be performed with the NBLAST program, score=100, wordlength-12 to obtain nucleotide sequences homologous to the nucleic acid molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In other embodiments, the monocyte-targeting aptamer described herein may contain up to 8 (e.g., up to 7, 6, 5, 4, 3, 2, or 1) nucleotide variations as compared to the nucleotide sequence of SEQ ID NO:1 or SEQ ID NO:2. Positions where such variations can be introduced can be determined based on, e.g., the reference nucleotide sequence of the targeted monocyte.

Any of the monocyte-targeting aptamers disclosed herein may contain up to 200 nucleotides (nts), e.g., 150 nts, 100 nts, 80 nts, 70 nts, 60 nts. 50 nts, 40 nts, or 30 nts. In some examples, the monocyte-targeting aptamer may contain nucleotides ranging from 30-150 nts, 30-100 nts, 30-80 nts, 30-70 nts, 30-60 nts, 30-50 nts, or 30-40 nts.

The monocyte-targeting aptamer may specifically bind human monocyte. Alternatively, the aptamer may bind to monocytes from different species (e.g., human and mouse).

In some embodiments, the monocyte-targeting aptamers described herein may contain non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the aptamer described herein has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3',5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

In another example, the monocyte-targeting aptamers described herein include one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted C1 to C10 alkyl or C2 to C10 alkenyl and alkynyl. They may also include at their 2' position heterocycloalkyl, heterocycloalkaryl, aminoalkylamino, polyalkylamino, substituted silyl, a RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

Alternatively or in addition, monocyte-targeting aptamers described herein may include one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of aptamer molecules to their targeting sites. These include 5-substituted pyrimidines, 6-azapyrimidines and N-2, N-6 and 0-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the monocyte-targeting aptamers described herein can be prepared by conventional methods, e.g., chemical synthesis or in vitro transcription. Their intended bioactivity as described herein can be verified by, e.g., those described in the Examples below. Vectors for expressing any of the monocyte-targeting aptamers are also within the scope of the present disclosure.

Any of the monocyte-targeting aptamers described herein may be conjugated to one or more polyether moieties, such as polyethylene glycol (PEG) moieties, via covalent linkage, non-covalent linkage, or both. Accordingly, in some embodiments, monocyte-targeting aptamers described herein can be pegylated. The disclosure is not meant to be limiting with respect to a PEG moiety of a specific molecular weight. In some embodiments, the polyethylene glycol moiety has a molecular weight ranging from 5 kDa to 100 kDa, lOkDa to 80 kDa, 20 kDa to 70 kDa, 20 kDa to 60 kDa, 20 kDa to 50 kDa, or 30 kDa to 50 kDa. In some examples, the PEG moiety has a molecular weight of 40 kDa. The PEG moiety conjugated to the monocyte-targeting aptamer described herein can be linear or branched. It may be conjugated to the 5' end of the nucleic acid aptamer, the 3' end of the aptamer, or both. When needed, the PEG moiety can be conjugated to the 3' end of the nucleic acid aptamer covalently.

Methods for conjugating PEG moieties to nucleic acids are known in the art and have been described previously, for example, in PCT Publication No. WO 2009/073820, the relevant teachings of which are incorporated by reference herein. It should be appreciated that the PEG conjugated nucleic acid aptamers and methods for conjugating PEG to the nucleic acid aptamers described herein, are exemplary and not meant to be limiting.

Aptamer-Based Lipid Nanoparticle Monocyte Targeting Systems

The present disclosure also provides lipid nanoparticles having any of the monocyte-specific nucleic acid aptamers attached on their surfaces. The lipid nanoparticles may comprise one or more suitable agents such as diagnostic agents or therapeutic agents. Due to the monocyte-targeting activity of the nucleic acid aptamers, the lipid nanoparticles disclosed herein can serve as an aptamer-based lipid nanoparticle monocyte targeting system, thereby using monocytes as a vesicle to deliver the agents associated with the lipid nanoparticles to a suit of interest, for example, a diseased or injured site.

(i) Lipid Nanoparticles Carrying Monocyte-Specific Nucleic Acid Aptamers

The aptamer-based lipid nanoparticle monocyte targeting systems described herein can comprise a [ ]suitable any lipid nanoparticle and one or more monocyte-targeting aptamers as disclosed herein (e.g., J10), which may be displayed on the surface of the nanoparticle. At least a portion of the monocyte-targeting aptamer may be exposed on the surface of the lipid nanoparticle such that the aptamer can interact with a binding partner, for example, the surface of circulating blood cells such as a monocyte. In some embodiments, the ratio between the lipids in the liposome and the monocyte-targeting aptamer (s) ranges from 1,000,000:1 to 30:1 (w/w). In some examples, the ratio is 1,000:1, 30:1 to 50:1 (w/w), e.g., 30:1 to 40:1 or 40:1 to 50:1.

The monocyte-targeting aptamer conjugated lipid nanoparticles (LNPs) described herein are capable of binding to monocytes, neutrophils, and/or other circulating blood cells that could migrate to an injured site. In some embodiments, the LNPs specifically bind to monocytes as relative to other types of cells such as endothelial cells. A LNP that "specifically binds" to a target cell such as monocyte is a term well understood in the art, and methods to determine such specific binding are also well known in the art. A LNP is said to exhibit "specific binding" activity to a target cell such as monocyte if it reacts or associates more frequently, more rapidly, with greater duration and/or with greater affinity with the target cell than it does with alternative target cells (e.g., endothelial cells). A LNP "specifically binds" to monocytes if it binds with greater affinity, avidity, more readily, and/or with greater duration than it binds to other types of cells such as endothelial cells. It is also understood by reading this definition that, for example, a LNP that specifically binds to a first target cell may or may not specifically or preferentially bind to a second target cell. As such, "specific binding" or "preferential binding" does not necessarily require (although it can include) exclusive binding. Generally, but not necessarily, reference to binding means preferential binding. In some specific examples, the LNP described herein does not bind to endothelial cells and thus does no induce thrombosis, i.e., the LNP binds to endothelial cells at no or a substantially low level such that the binding, if any, is not sufficient to induce significant thrombosis (e.g., clinical meaningful thrombosis, which can be determined by routine medical assays).

In some instances, the lipid nanoparticle disclosed herein may be a liposome, on which one or more monocyte-targeting aptamers can be surface displayed. The term "liposome" as used herein refers to a composition comprising an outer lipid layer membrane (e.g., a single lipid bi-layer known as unilamellar liposomes or multiple lipid bi-layers known as multilamellar liposomes) surrounding an internal aqueous space. See, e.g., Cullis et al., *Biochim. Biophys Acta,* 559: 399-420 (1987). A unilamellar liposome generally has a diameter in the range of about 20 to about 400 nanometers (nm), about 50 to about 300 nm, about 300 to about 400 nm, or about 100 to about 200 nm. A multilamellar liposome usually has a diameter in the range of about one to about ten micrometers and may comprise anywhere from two to hundreds of concentric lipid bilayers alternating with layers of an aqueous phase.

Each of the lipid bi-layers may comprise two monolayers containing oppositely oriented amphipathic lipid molecules. Amphipathic lipids typically comprise a polar (hydrophilic) headgroup covalently linked to one or more non-polar (hydrophobic) acyl or alkyl chains. Energetically unfavorable contacts between the hydrophobic acyl chains and a surrounding aqueous medium induce amphipathic lipid molecules to arrange themselves such that polar headgroups are oriented towards the bilayer's surface and acyl chains are oriented towards the interior of the bilayer, effectively shielding the acyl chains from contact with the aqueous environment.

One or more naturally occurring and/or synthetic lipid compounds may be used in the preparation of the liposomes described herein. The liposomes may contain negatively charged lipids, positively charged lipids, or a combination thereof. Examples of suitable negatively charged lipids include, but are not limited to dimyrystoyl,-dipalmitoyl- and distearoylphasphatidylglycerol, dimyrystoyl,-dipalmitoyl- and dipalmitoylphosphatidic acid, dimyrystoyl,-dipalmitoyl- and dipalmitoylphosphatidylethanolamine, their unsaturated diacyl and mixed acyl chain counterparts as well as cardiolipin. Examples of positively charged lipids include, but are not limited to, N,N'-dimethyl-N,N'-dioctacyl ammonium bromide (DDAB) and chloride DDAC), N-(1-(2,3-dioleyloxy)propyl)-N,N,N-trimethylammonium chloride (DOTMA), 3.beta.-[N—(N',N'-dimethylaminoethyl) carbamoyl) cholesterol (DC-chol), 1,2-dioleoyloxy-3-[trimethylammonio]-propane (DOTAP), 1,2-dioctadecyloxy-3-[trimethylammonio]-propane (DSTAP), and 1,2-dioleoyloxypropyl-3-dimethyl-hydroxyethyl ammonium chloride (DORI) and cationic lipids described in e.g. Martin et al., *Current Pharmaceutical Design* 2005, 11, 375-394. Examples of suitable neutral charged lipids include, but are not limited to DLPC (1,2-dilauroyl-sn-glycero-3-phosphocholine), DMPC (1,2-dimyristoyl-sn-glycero-3-phosphocholine), DPPC (1,2-dipalmitoyl-sn-glycero-3-phosphocholine), DSPC (1,2-distearoyl-sn-glycero-3-phosphocholine), DOPC (1,2-dioleoyl-sn-glycero-3-phosphocholine), DMPA (Sodium 1,2-ditetradecanoyl-sn-glycero-3-phosphate), DPPE (1,2-Dipalmitoyl-sn-glycero-3-phosphoethanolamine), and DOPE (1,2-dioleoyl-sn-glycero-3-phosphoethanolamine).

In some embodiments, the liposome described herein can be prepared using one or more phospholipids, and optionally one or more additional molecules of similar molecular shape and dimensions having both a hydrophobic moiety and a hydrophilic moiety (e.g., cholesterol). Suitable phospholipids for use in preparing the liposomes described herein include, but are not limited to, phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol. Additional nonphosphorous-containing lipids include, but are not limited to, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, diacylglycerolsuccinate, and the like.

In some embodiments, the major lipid component of the liposomes described herein can be phosphatidylcholine, which may have a variety of acyl chain groups of varying chain length and degree of saturation. In some examples, the phosphatidylcholines contain saturated fatty acids with carbon chain lengths in the range of, e.g., $C_{14}$ to $C_{22}$. Saturated long-chain phosphatidylcholines are less permeable and more stable in vivo than their unsaturated counterparts. Phosphatidylcholines with mono- or di-unsaturated fatty acids and mixtures of saturated and unsaturated fatty acids may also be used.

Any of the liposomes described herein may further comprise a sterol, preferably cholesterol, at molar ratios ranging from about 0.1 to 1.0 (cholesterol:phospholipid). In some examples, the liposomes may comprise a combination of distearoylphosphatidylcholine/cholesterol, dipalmitoylphosphatidylcholine/cholesterol, dimyrystoylphosphatidylcholine/cholesterol, 1,2-Dioleoyl-sn-glycero-3-phosphocholine (DOPC)/cholesterol, or egg sphingomyelin/cholesterol.

When needed, the liposomes described herein may be coated with a polymer layer to enhance stability of the liposomes in vivo (e.g., sterically stabilized liposomes). Examples of suitable polymers include, but are not limited to, poly(ethylene glycol), which may form a hydrophilic surface layer that improves the circulation half-life of liposomes and enhances the amount of liposomes that reach therapeutic targets. See, e.g., Working et al. J Pharmacol Exp Ther, 289: 1128-1133 (1999); Gabizon et al., J Controlled Release 53: 275-279 (1998); AdlakhaHutcheon et al., Nat Biotechnol 17: 775-779 (1999); and Koning et al., Biochim Biophys Acta 1420: 153-167 (1999). Examples of useful PEG-lipids for use in making the liposomes described herein include, but are not limited to, 1,2-Diacyl-sn-Glycero-3-Phosphoethanolamine-N-[Methoxy(Polyethylene glycol)-350](mPEG 350 PE); 1,2-Diacyl-sn-Glycero-3-Phosphoethanolamine-N-[Methoxy(Polyethylene glycol)-550](mPEG 550 PE); 1,2-Diacyl-sn-Glycero-3-Phosphoethanolamine-N-[Methoxy(Polyethylene glycol)-750](mPEG 750 PE); 1,2-Diacyl-sn-Glycero-3-Phosphoethanolamine-N-[Methoxy(Polyethylene glycol)-1000](mPEG 1000 PE); 1,2-Diacyl-sn-Glycero-3-Phosphoethanolamine-N-[Methoxy(Polyethylene glycol)-2000](mPEG 2000 PE); 1,2-Diacyl-sn-Glycero-3-Phosphoethanolamine-N-[Methoxy(Polyethylene glycol)-3000](mPEG 3000 PE); 1,2-Diacyl-sn-Glycero-3-Phosphoethanolamine-N-[Methoxy(Polyethylene glycol)-5000](mPEG 5000 PE); N-Acyl-Sphingosine-1-[Succinyl (Methoxy Polyethylene Glycol) 750](mPEG 750 Ceramide); N-Acyl-Sphingosine-1-[Succinyl(Methoxy Polyethylene Glycol) 2000](mPEG 2000 Ceramide); and N-Acyl-Sphingosine-1-[Succinyl(Methoxy Polyethylene Glycol) 5000](mPEG 5000 Ceramide).

A variety of methods can be used for preparing the liposomes described herein. Such methods are known in the art or disclosed herein, for example, the methods described in Lichtenberg and Barenholz in Methods of Biochemical Analysis, Volume 33, 337-462 (1988). See also Szoka et al., Ann. Rev. Biophys. Bioeng. 9:467 (1980); U.S. Pat. Nos. 4,235,871, 4,501,728, and 4,837,028; Liposomes, Marc J. Ostro, ed., Marcel Dekker, Inc., New York, 1983, Chapter 1; and Hope, et al., Chem. Phys. Lip. 40:89 (1986), the relevant disclosures of each of which are incorporated herein by reference. Small unilamellar vesicles (SUV, size <100 nm) can be prepared by a combination of standard methods of thin-film hydration and repeated extrusion as described before (Tseng et al., 1999).

Conventional techniques are available for sizing liposomes to a desired size. See, e.g., U.S. Pat. No. 4,737,323, and Hope et al., Biochim. Biophys. Acta, 812: 55-65 (1985), the relevant disclosures of each of which are incorporated by reference. Sonicating a liposome suspension either by bath or probe sonication produces a progressive size reduction down to small unilamellar vesicles less than about 50 nm in size. Homogenization or microfluidization are other methods which rely on shearing energy to fragment large liposomes into smaller ones. In a typical homogenization procedure, multilamellar vesicles are recirculated through a standard emulsion homogenizer until selected liposome sizes, typically between about 100 and 500 nm, are observed. In both methods, the particle size distribution can be monitored by conventional laser-beam particle size discrimination.

Extrusion of liposomes through a small-pore polycarbonate membrane or an asymmetric ceramic membrane is a very effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size.

Any of the liposomes described herein can be analyzed by conventional methods to determine its physical and/or chemical features. For example, a phosphate assay can be used to determine liposome concentration. One phosphate assay is based on the interaction between molybdate and malachite green dye. The main principle involves the reaction of inorganic phosphate with molybdate to form a colorless unreduced phosphomolybdate complex which is converted to a blue colored complex when reduced under acidic conditions. Phosphomolybdate gives 20 or 30 times more color when complexed with malachite green. The final product, reduced green soluble complex is measured by its absorbance at 620 nm and is a direct measure of inorganic phosphate in solution.

In other embodiments, the particles for drug delivery as described herein can be nanoparticles made of one or more polymers or co-polymers. For example, the nanoparticles can be poly(lactic-co-glycolic acid) (PLAG) nanoparticles, which can be prepared by routine technology.

Any of the monocyte-specific nucleic acid aptamers disclosed herein may be conjugated to the lipid nanoparticle via a conventional approach. For example, a docking nucleic acid fragment may be attached to the lipid nanoparticle. The docking nucleic acid fragment comprises a nucleotide sequence complementary to a portion of the monocyte-specific nucleic acid aptamer, e.g., the anchor nucleic acid fragment or a portion thereof. Via base pairing, the aptamer can be attached to the lipid nanoparticle.

To conjugate a docking nucleic acid fragment, one or more naturally occurring and/or synthetic lipid compounds used in the preparation of the liposomes described herein may have at least one activated terminal group, which may react with the docking nucleic acid fragment. Examples of end-group forms of lipid compound derivatives include methylation, carboxylation, amination, and maleylation. In some examples, lipid compounds used in the preparation of the liposomes described herein may be carboxyl-terminated, amino-terminated, hydrazide-terminated, or maleimide-terminated lipids. In some examples, lipid compounds used in the preparation of the liposomes described herein may be N-(5'-hydroxy-3'-oxypentyl)-10-12-pentacosadiynamide (h-PEG1-PCDA), N-(5'-sulfo-3'-oxypenty 1)-10-12-pentacosadiynamide (sulfo-PEG1-PCDA), N-[methoxy(polyethylene glycol)-750]-10-12-pentacosadiynamide (m-PEG750-PCDA), N-[maleimide(polyethylene glycol)-1500]-10-12-pentacosadiynamide (mal-PEG1500-PCDA), 1,2-distearoyl-sn-glycero-3-phosphoethanolamine-N-[maleimide(polyethylene glycol)-2000](Mal-PEG-DSPE), L-a-phosphatidylcholine hydrogenated soy (hydrogenated soy PC), distearoylphosphatidylcholine (DSPC), cholesterol, 1,2-distearoyl-sn-glycero-3-phosphoethanolamine-N-[methoxy(polyethylene glycol)-2000](m-Peg2000-DSPE), and combinations thereof.

A docking nucleic acid may be attached to the lipid nanoparticle via reaction with the activated terminal group noted above. In some examples, the docking nucleic acid may be modified to add a reactive group, for example, a thiol group. Such a docking nucleic acid may react with an activated terminal group on the lipids to form a covalent bond.

In some examples, docking nucleic acid fragment disclosed herein may be attached to an activated the terminal group of the lipid compounds derivatives described herein via a conjugation technique. Examples of suitable conjugation techniques include carbonyl addition-elimination/reductive amination, amidation, maleimide-thiol coupling, glutaraldehyde crosslinking, isothiocyanate-amine coupling, hydrazone coupling, oxime coupling, Schiff base formation/reduction, aqueous Diels-Alder and "Click" chemistries. In some examples, a docking nucleic acid fragment described herein is conjugated to a lipid compound derivative described herein by incubating the two in the presence of a reducing agent. In some examples, conjugation of a docking nucleic acid fragment described herein to a lipid compound derivative described herein occurs when the molar ratio of docking nucleic acid fragment to reducing agent to lipid compound derivative to is about 1:10:20. In some examples, conjugation of a docking nucleic acid fragment described herein to a lipid compound derivative described herein is about 70% to about 100% efficient.

In some embodiments, the monocyte-targeting aptamer disclosed herein may be hybridized to a LNP disclosed herein via a docking nucleic acid fragment conjugated to lipids that comprise the LNP. In some examples, a docking nucleic acid fragment interacts with a monocyte-targeting aptamer disclosed herein, the monocyte-targeting aptamer comprising an anchor nucleic acid fragment that corresponds to the docking nucleic acid fragment. In some examples, the monocyte-targeting aptamer hybridizes to LNPs comprising lipids conjugated a docking nucleic acid fragment by incubation for about 8 hours to about 18 hours. In some examples, the ratio of LNPs comprising a docking nucleic acid fragment to a monocyte-targeting aptamer during incubation may be about 1:0.25, 1:0.5, 1:1.25, 1:1.50, 1:1.75, 1:2, 1:2.5, 1:3, 1:4, or 1:5. In some examples, hybridization of the docking nucleic acid fragment to the monocyte-targeting aptamer disclosed herein can be about 8% to about 85% efficient.

(ii) Therapeutic Agents and Diagnostic Agents

Any of the monocyte-targeting aptamer labeled lipid nanoparticles (LNPs) described herein may encapsulate a therapeutic agent. Alternatively, any of the monocyte-targeting aptamer labeled lipid nanoparticles (LNPs) described herein may encapsulate a diagnostic agent. In some examples, the therapeutic agent encapsulated by any of the monocyte-targeting aptamer labeled lipid nanoparticles (LNPs) described herein may be an agent for treating a heart injury, which optionally is a heart ischemia reperfusion injury, and/or wherein the diagnostic agent is for diagnosing a heart injury.

In some examples, a therapeutic agent encapsulated by any of the monocyte-targeting aptamer labeled lipid nanoparticles (LNPs) described herein may be a cardio-protective agent, an anti-inflammatory agent, an anti-apoptotic agent, an anti-fibrotic agent, an immuno-modulatory agent, a hypoxic response stimulator, or a proangiogenic agent.

Anti-inflammatory agents are compounds capable of suppressing inflammation. Examples include, but are not limited to non-steroidal anti-inflammatory drugs (NASIDs) such as aspirin, ibuprofen, and naproxen. Other examples include alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

Anti-apoptotic or cardio-protective agents are proteins, nucleic acids, or small molecule compounds that can inhibit apoptosis. Examples include IGFs, PDGFs, neuregulins, and angiopoietins.

Proangiogenic agents as used herein refer to chemical compounds (e.g., proteins, nucleic acid or small molecule compounds) that functions to stimulate the development of new blood vessels. The proangiogenic agent described herein can be a growth factor or cytokine that induces or promotes angiogenesis by stimulating endothelial cell growth or migration, for example, vascular endothelial growth factor (VEGF). Alternatively, the pro-angiogenic agent can be a member of the fibroblast growth factor (FGF) family such as FGF-1 (acidic), FGF-2 (basic), FGF-4 or FGF-5. Examples include trafermin, GENERX™, or an adenoviral gene therapy vector encoding FGF-4. Additional pro-angiogenic agents include angiopoietin-1. Specific examples of the proangiogenic agents for use in the present disclosure include, but are not limited to, VEGFs, FGFs, angiopoietins, and PDGFs.

Anti-fibrotic agents refer to chemical compounds (e.g., proteins, nucleic acids, or small molecule compounds) that have inhibitory activities against fibrosis, including abnormal formation of fibrous connective tissue, which is typically comprises of collagen. The anti-fibrotic agents described herein may have different mechanisms of action, e.g., reducing the formation of collagen or enhancing the metabolism or removal of collagen in the affected areas in the body. All such compounds having activity in the reduction of the presence of fibrous tissue are included herein, without regard to the particular mechanism of action by which each such drug functions. Examples include Nintedanib and Pirfenidone.

Immuno-modutory agents are proteins, nucleic acids, or small molecule compounds that can prevent or ameliorate undesired immune responses. Examples include Thalidomide, Lenalidomide, Pomalidomide, Apremilast and steroids.

Mitochondrial dysfunction inhibitors prevent mitochondrial dysfunction during myocardial injury, by affecting at least ETC (electron transport chain) and OXPHOS (oxidative phosphorylation) processes and mitochondrial dynamics and inducing mPTP (mitochondrial permeability transition pore) opening. Non-limiting examples of mitochondrial dysfunction inhibitors include: L-carnitine, vitamins C and E, Mito-Q10, edaravone, elamipretide (SS-31), miR145, melatonin, bendavia peptide, panolazine, and propofol.

In some embodiments, therapeutic agents may be a drug commonly used for treatment of patients with heart failure with reduced ejection fraction. In some aspects, a therapeutic agent can be an angiotensin-converting enzyme (ACE) inhibitor. Examples of ACE inhibitors suitable for use as disclosed herein include Captopril, Enalapril, Fosinopril, Lisinopril, Perindopril, Quinapril, Ramipril, Trandolapril, benazepril (Lotensin), ramipril (Altace), captopril, and a combination thereof. In other aspects, a therapeutic agent can be an aldosterone antagonist. Examples of aldosterone antagonists suitable for use as disclosed herein include Spironolactone and Eplerenone. In some other aspects, a therapeutic agent can be an angiotensin receptor blocker (ARB). Examples of angiotensin receptor blockers suitable for use as disclosed herein include Candesartan, Losartan, Valsartan, losartan (Cozaar), olmesartan (Benicar), valsartan (Diovan), and a combination thereof. In other aspects, a therapeutic agent can be an angiotensin receptor-neprilysin inhibitor (ARNI). An example of an ARNI suitable for use as disclosed herein include Sacubitril/valsartan. In some aspects, a therapeutic agent can be a beta blocker. Examples of angiotensin receptor blockers suitable for use as disclosed herein include Bisopolol, Carvedilol, Carvedilol CR, Metoprolol succinate extended release (Metoprolol CR/XL), labetalol (Trandate), propranolol (Inderal), and a combination thereof. In some aspects, a therputic agent can be an $I_f$ ion channel inhibitor. An example of a an $I_f$ ion channel inhibitor includes Ivabradine.

Exemplar therapeutic agents may be a hypoxic response stimulator agent. Hypoxic response stimulator agents stabilize at least one hypoxia inducible factor (HIF) and induce at least one hypoxic response. Examples of hypoxic response stimulator agents include, but are not limited to: hypoxia mimetic agents (e.g., $Fe^{2+}$ substitutes ($Co^{2+}$, $Ni^{2+}$)); 2-oxoglutarate mimics (e.g., dimethyloxalylglycine, N-oxalylglycine and N-oxalyl-D-phenylalanine); $Fe^{2+}$ chelators (e.g., deferoxamine also known as desferrioxamine, and AKB-4924); inhibitors of PHD enzymes such as PHD2 (e.g., IOX2, MK-8617, 2-methoxyestradiol, AKB-4924, IOX3 (FG-2216), FG-4497, roxadustat (FG-4592) Vadadustat (AKB-6548), Daprodustat (GSK1278863), Desidustat (ZYAN-1), Molidustat (Bay 85-3934) IOX4, Enarodustat (JTZ-951)); inhibitors of cullin neddylation (e.g., MLN4924); proteasome inhibitors, and a VHL:HIF protein-protein interaction blocker (e.g., VH298). In some embodiments, therapeutic agents may be any of the compounds found in Table 1.

TABLE 1

| IOX2 Related Drugs | | | |
|---|---|---|---|
| Drug | Molecular Weight (MW) | Chemical Structure | Description |
| IOX2 | 352.34 | 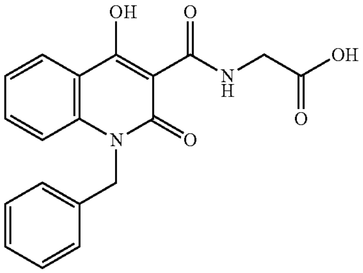 [SMILES: O=C(O)CNC(=O)c1c(O)c2ccccc2n(Cc2ccccc2)c1=O] | HIF-1α prolyl hydroxylase-2 (PHD2) inhibitor |
| FG-2216 (IOX3) | 280.66 | 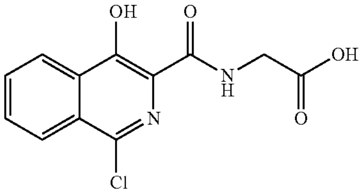 [SMILES: O=C(O)CNC(=O)c1nc(Cl)c2ccccc2c1O] | FG-2216 is a potent, and orally active HIF prolyl 4-hydroxylase inhibitor for PHD2. Phase 2. |
| IOX4 | 328.33 | 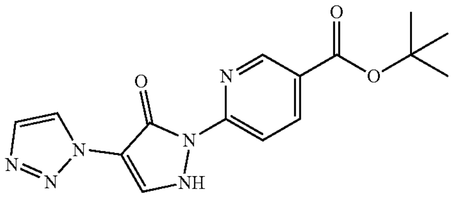 [SMILES: CC(C)(C)OC(=O)c1ccc(-n2[nH]cc(-n3ccnn3)c2=O)nc1] | IOX4 is a selective HIF prolyl-hydroxylase 2 (PHD2) inhibitor, induces HIFα in cells and in wildtype mice with marked induction in the brain tissue. IOX4 competes with and displaces 2-oxoglutarate (20G) at the active site of PHD2. |
| Roxadustat (FG-4592) | 352.34 | 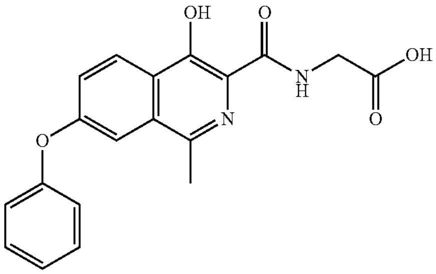 [SMILES: Cc1nc(C(=O)NCC(=O)O)c(O)c2ccc(Oc3ccccc3)cc12] | Roxadustat (FG-4592) is an HIF-α prolyl hydroxylase inhibitor, which stabilizes HIF-2 and induces EPO production. Phase 3 |
| MK-8617 | 443.45 | 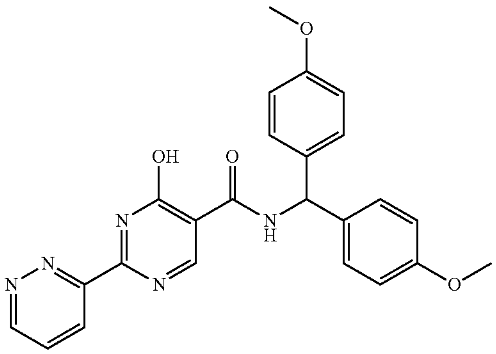 [SMILES: COc1ccc(C(NC(=O)c2cnc(-c3cccnn3)nc2O)c2ccc(OC)cc2)cc1] | MK-8617 is an orally active pan-inhibitor of Hypoxia-inducible factor prolyl hydroxylase 1-3 (HIF PHD1-3), inhibiting −PHD1, −2, −3 |

TABLE 1-continued

| IOX2 Related Drugs | | | |
|---|---|---|---|
| Drug | Molecular Weight (MW) | Chemical Structure | Description |
| Molidustat (BAY 85-3934) | 314.30 | 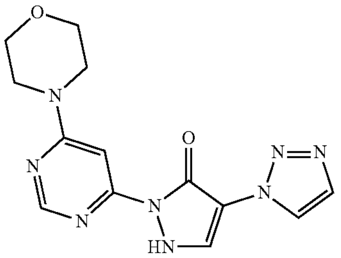 [SMILES: O=c1c(-n2ccnn2)c[nH]n1-c1cc(N2CCOCC2)ncn1] | Molidustat (BAY 85-3934) is a potent pan-inhibitor of hypoxia-inducible factor prolyl hydroxylase (HIF-PH), including PHD1, PHD2, and PHD. Phase 2. |
| Daprodustat (GSK1278863) | 393.43 | 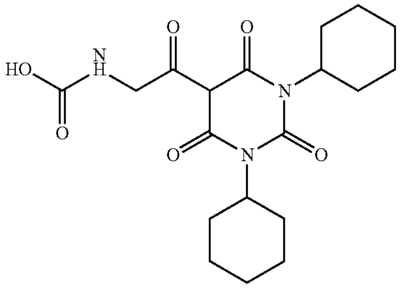 [SMILES: O=C(O)NCC(=O)C1C(=O)N(C2CCCCC2)C(=O)N(C2CCCCC2)C1=O] | Daprodustat (GSK1278863) is an orally administered hypoxia-inducible factor-prolyl hydroxylase (HIF-PH) inhibitor. Phase 2. |
| Vadadustat (AKB-6548) | 306.70 | 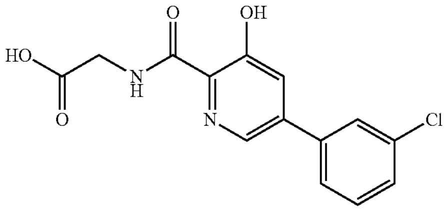 [SMILES: O=C(O)CNC(=O)c1ncc(-c2cccc(Cl)c2)cc1O] | Vadadustat is an orally active pan-inhibitor of Hypoxia-inducible factor prolyl hydroxylase (HIF PH) |
| Enarodustat (JTZ-951) | 340.33 | 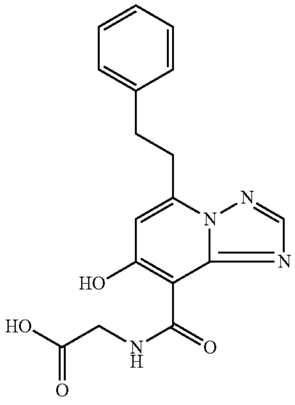 [SMILES: O=C(O)CNC(=O)c1c(O)cc(CCc2ccccc2)n2ncnc12] | Enarodustat is an orally active factor prolyl hydroxylase inhibitor; Enarodustat has entered clinical trial for renal anemia. |

Exemplar diagnostic agents may be a medical imaging agent, for example, a contrast agent, a radioactive agent, a radiopharmaceutical, an iron oxide particle, etc. Radioactive molecules suitable for in vivo imaging include, but are not limited to, $^{122}$I, $^{123}$I, $^{124}$I, $^{125}$I, $^{131}$I, $^{18}$F $^{75}$Br, $^{76}$Br, $^{77}$Br, $^{211}$At, $^{225}$Ac, $^{177}$Lu, $^{153}$Sm, $^{186}$Re, $^{188}$Re, $^{67}$Cu, $^{213}$Bi, $^{212}$Bi, $^{212}$Pb, and $^{67}$Ga.

Exemplary radiopharmaceuticals suitable for in vivo imaging include $^{111}$In oxyquinoline, $^{131}$I sodium iodide, $^{99}$mTc mebrofenin, and $^{99}$mTc red blood cells, $^{123}$I sodium iodide, $^{99}$mTc exametazime, $^{99}$mTc macroaggregate albumin, $^{99}$mTc medronate, $^{99}$mTc mertiatide, $^{99}$mTc oxidronate, $^{99}$mTc pentetate, $^{99}$mTc pertechnetate, $^{99}$mTc sestamibi, $^{99}$mTc sulfur colloid, $^{99}$mTc tetrofosmin, Thallium-201, and Xenon-133. The diagnostic agent can also be a dye, e.g., a fluorophore, which is useful in detecting a disease site such as a heart injury site in a subject.

Any of the therapeutic agents or diagnostic agents as described herein can be incorporated into a suitable liposome as also described herein by a conventional method or a method described herein. In some embodiments, liposomes can be loaded by imposing a pH gradient across the liposome membrane (wherein the liposome interior is acidic) and incubating the liposome with the therapeutic agent or diagnostic agent to be encapsulated, as described, e.g., in Maurer et al., Expert Opinion in Biological Therapy 1, 923-47; NBoman et al., Cancer Res. 54, 2830-2833; Waterhouse et al., Methods Enzymol. 391 (2005) 40-57, hereby incorporated by reference for the intended purposes. This method is understood to mean "active loading" as used in the art. In some examples, the pH gradient can be an ammonium sulfate gradient, as described generally in Haran et al., Biochim. Biophys. Acta 1115 (1993) 201-215 and U.S. Pat. No. 5,316,771, hereby incorporated by reference for the intended purposes. Once the therapeutic agent or diagnostic agent has been loaded into the liposomes, the compositions can be used directly, or the composition can be further treated to remove any unloaded drug.

pH loading techniques generally involve two steps, the generation of the pH gradient with low intra-liposomal pH and the subsequent loading of the therapeutic agent or the diagnostic agent. Transmembrane proton gradients can be generated by a variety of ways. For example, liposomes can be prepared in a low pH buffer such as a pH 4 citrate buffer followed by exchange of the external buffer solution against a pH 7.5 buffer (e.g. Madden et al., Chem. Phys. Lipids, 53:37-46 (1990)). Alternatively, ionophores can be used in conjunction with cation gradients (high internal cation concentrations) (e.g., Fenske et al., Biochim Biophy. Acta, 1414:188-204 (1998)). Ionophores such as nigericin and A23187 couple the outward movement of monovalent or divalent cations, respectively, to the inward movement of protons thus acidifying the interior of the liposomes. Furthermore, liposomes can be prepared in the presence of high concentrations of a weak base such as ammonium sulfate (Haran et al., Biochim. Biophys. Acta, 1151:201-215 (1993)). Removal of the external ammonium salt solution results in the generation of a pH gradient according to the same principle, which is also responsible for the subsequent drug loading process.

In addition to pH gradients, metal ion gradients can also be used for active loading of a therapeutic agent or diagnostic agent. See, for example, Cheung et al., *Biochim Biophys Acta,* 1414:205-216 (1998). The neutral form of the weak base therapeutic agent or diagnostic agent can permeate across the membrane and is retained in the aqueous interior of the liposomes through formation of a drug-metal ion complex.

If the therapeutic agent or diagnostic agent is a water-soluble weak base drug, it may be dissolved in an aqueous solution (e.g., 300 mM sucrose, or isotonic buffer solutions with appropriate pH), combined with the liposome suspension and then incubated at a suitable temperature. The drug solution can contain a small amount of a water-miscible organic solvent to increase the solubility of the drug (e.g., <10% ethanol). The incubation temperature and time depend on the lipid composition and the nature of the drug. Typically, liposomes composed of cholesterol and long-chain saturated fatty acids such as DSPC/cholesterol are less permeable than liposomes formed from short-chain saturated lipids (e.g., DMPC/cholesterol) or unsaturated lipids and require higher temperatures to achieve rapid and efficient loading. For example, DSPC/cholesterol liposomes typically require temperatures equal or higher than 60° C.; loading is typically complete after 5-15 minutes, but may take up to 2 hours.

If the therapeutic agent or diagnostic agent is lipophilic, the agent can be mixed with the lipids for making the liposome under conditions that allow for distribution of the agent between the two monolayers of the liposome bilayer. The agent in the external monolayer can then be loaded into the liposome interior (flipped to the inner monolayer of the LN bilayer) in response to a trans-membrane pH or other ion gradient using the methods described herein.

Remote loading of compounds into liposomes employs formation of transmembrane gradients as described in Ceh et al., Biochim Biophys Acta. 1995 Nov. 1; 1239(2):145-56. This method includes incubating the therapeutic agent or diagnostic agent to be loaded into the liposomes and a boronic acid compound with suspended liposomes, thereby achieving accumulation of the therapeutic agent or diagnostic agent within the liposomes (Ceh et al., 1995 and U.S. Pat. No. 6,051,251).

Pharmaceutical Compositions and Uses Thereof

Any of the monocyte-targeting lipid nanoparticles disclosed herein, comprising one or more therapeutic agents or diagnostic agents, can be mixed with a pharmaceutically acceptable carrier to form a pharmaceutical composition for use, e.g., in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. See, e.g., Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The present disclosure also provides pharmaceutical compositions comprising any of the monocyte-targeting aptamer conjugated lipid nanoparticles (LNPs) described herein, which may encapsulate one or more of the therapeutic or diagnostic agents also described herein, and a pharmaceutically acceptable carrier or excipient. The carrier in the pharmaceutical composition must be "acceptable" in the sense that it is compatible with the active ingredient of the composition, and preferably, capable of stabilizing the active ingredient and not deleterious to the subject to be treated.

Suitable carriers or excipients for the pharmaceutical compositions disclosed herein may be a substance that enhances the ability of the body of an individual to absorb the LNP, facilitate binding of the LNP to monocytes, and/or enhance endocytosis of the LNP by macrophages developed from the monocytes. Suitable carriers and/or excipients also include any substance that can be used to bulk up formulations with a modified LNP herein described, to allow for convenient and accurate dosage. In addition, carriers and/or excipients may be used in the manufacturing process to aid in the handling of a LNP described herein. Depending on the route of administration, and form of medication, different carriers and/or excipients may be used. Exemplary excipients include but are not limited to antiadherents, binders, coatings disintegrants, fillers, flavors (such as sweeteners) and colors, glidants, lubricants, preservatives, sorbents. Carriers and/or excipients described herein may also include vehicles and/or diluents, wherein: "vehicles" indicates any of various media acting usually as solvents or carriers; "diluent" indicates a diluting agent which is issued to dilute an active ingredient of a composition; suitable diluent include any substance that can decrease the viscosity of a medicinal preparation.

The type and amounts of carriers and/or excipients are chosen in function of the chosen pharmaceutical form; suitable pharmaceutical forms are liquid systems like solutions, infusions, suspensions; semisolid systems like colloids, gels, pastes or cremes; solid systems like powders, granulates, tablets, capsules, pellets, microgranulates, minitablets, microcapsules, micropellets, suppositories; etc. Each of the above systems can be suitably be formulated for normal, delayed or accelerated release, using techniques well-known in the art.

Pharmaceutical compositions comprising the monocyte-targeting LNPs described herein, comprising one or more therapeutic agents or diagnostic agents, can be prepared according to standard techniques, as well as those techniques described herein. In some examples, the pharmaceutical compositions are formulated for parenteral administration, including intracanalicular administration, intravenous administration, subcutaneous administration, or intramuscular administration. In some examples, the pharmaceutical compositions are administered intravenously by a bolus injection or infusion. Suitable formulations for use in the present invention are found in Remington's Pharmaceutical Sciences, Mack Publishing Company, Philadelphia, Pa., 17th ed. (1985).

In some examples, the pharmaceutical composition is formulated for injection, such as intravenous infusion. A sterile injectable composition, e.g., a sterile injectable aqueous or oleaginous suspension, can be formulated according to techniques known in the art using suitable dispersing or wetting agents (such as Tween 80) or suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically.

Any of the pharmaceutical compositions can be used for delivering a therapeutic agent or diagnostic agent to a desired target site using circulating monocytes as carriers. To practice this use, an effective amount of a pharmaceutical composition comprising any monocyte-targeting aptamers or linker conjugates thereof and a therapeutic agent or diagnostic agent can be administered to a subject in need of the treatment (e.g., a human subject) via a suitable route, such as those described herein. Also to practice this use, an effective amount of a pharmaceutical composition comprising any of the LNPs described herein, which encapsulates a therapeutic agent (e.g., an anti-inflammatory agent) or a diagnostic agent, can be administered to a subject in need of the treatment (e.g., a human subject) via a suitable route, such as those described herein. Via the binding activity to monocytes, the LNPs would be associated with circulating monocytes of the subject and be delivered to a site where monocytes accumulate (e.g., a site where inflammation occurs). Once the monocytes cross the endothelial cell layers, they differentiate into macrophages, which absorb the associated LNPs via endocytosis, thereby releasing the entrapped therapeutic agent or diagnostic agent to exert its therapeutic or diagnostic effects.

"An effective amount" as used herein refers to the amount of each active agent required to confer therapeutic effects on the subject, either alone or in combination with one or more other active agents. Effective amounts vary, as recognized by those skilled in the art, depending on route of administration, excipient usage, and co-usage with other active agents.

Such amounts will depend, of course, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

In some embodiments, the pharmaceutical composition, comprising a hypoxic response stimulating agent as described herein, is for use in treating an ischemic heart disease (IHD). The term "treating" as used herein refers to the application or administration of a composition including one or more active agents to a subject, who has an allergic disease, a symptom of the allergic disease, or a predisposition toward the allergic disease, with the purpose to cure, heal, alleviate, relieve, alter, remedy, ameliorate, improve, or affect the disease, the symptoms of the disease, or the predisposition toward the disease. Examples of IHD include, but are not limited to obstructive coronary artery disease, nonobstructive coronary artery disease, and coronary microvascular disease.

After being administered into a subject having, suspected of having, or at risk for an IHD, e.g., a human IHD patient, the LNP can be delivered to an infarct heart area via attaching to monocytes and to exert the desired therapeutic effects at the target site. IHD is a disease characterized by reduced blood supply to the heart due to, e.g., atherosclerosis. Symptoms associated with IHD include, but are not limited to, chest pain or discomfort.

Kits

The present disclosure also provides kits for use in delivering therapeutic agents or diagnostic agents to a target site or for use in treating an IHD by delivering an anti-IHD agent, such as a hypoxic response stimulating agent, to an infarct heart area. Such kits can include one or more containers comprising any of the pharmaceutical compositions described herein, which comprises a monocyte-targeting aptamer labeled lipid nanoparticles (LNPs) described herein or a nanoparticle alike encapsulating the therapeutic agent or diagnostic agent and a pharmaceutically acceptable carrier.

In some embodiments, the kit can comprise instructions for use in accordance with any of the methods described herein. The included instructions can comprise a description of administration of the pharmaceutical composition for delivering the therapeutic agent or diagnostic agent encapsulated therein or for treating an IHD according to any of the methods described herein. The kit may further comprise a description of selecting an individual suitable for treatment based on identifying whether that individual has, is suspected of having, or is at risk for IHD.

The instructions relating to the use of the pharmaceutical composition described herein, which comprises a LNP encapsulating a therapeutic agent or a diagnostic agent, generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for delivering the therapeutic agent or diagnostic agent to a target site or for treating an IHD. Instructions may be provided for practicing any of the methods described herein.

The kits as described herein are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

The kits described herein may optionally provide additional components such as buffers and interpretive information. Normally, the kit comprises a container and a label or package insert(s) on or associated with the container. In some embodiments, the present disclosure provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit, and scope of the present disclosure. All such modifications are intended to be within the scope of the disclosure.

Example 1. Development of Monocyte-Specific Aptamers

Figure 1B:
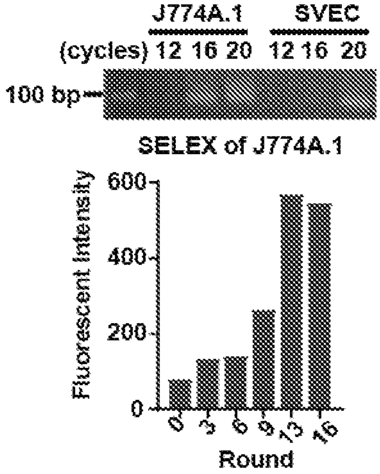
Figure 1C:
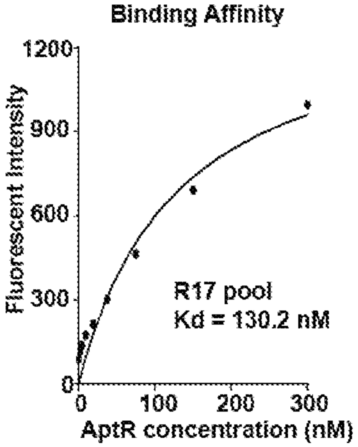
Figure 1D:
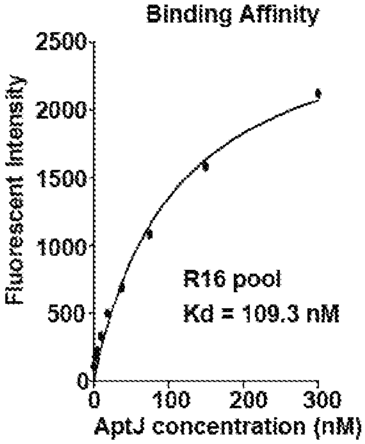
Figure 1E:
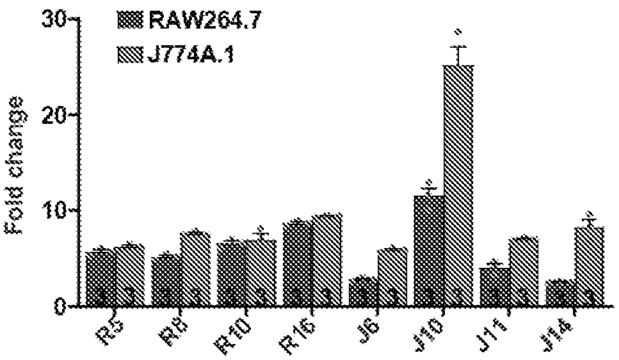

The cell-SELEX (systematic evolution of ligands by exponential enrichment) method was used to generate a DNA aptamer that can bind specifically to a monocyte. Briefly, ssDNA library containing $10^{15}$ sequences was incubated with $10^6$ positive cells of the murine monocyte cell line RAW264.7 or J774A.1 in SELEX buffer (150 mM NaCl, 5 mM KCl, 1 mM MgCl2, 1 mM $CaCl_2$ and 40 mM HEPES pH 7.4) supplemented with 0.1% (w/v) BSA and 1 mg/mL salmon sperm DNA at 37° C. for 30 minutes. The unbound ssDNA was removed by washing with SELEX buffer. Monocyte-targeting ssDNA was eluted at 95° C. for 10 minutes and amplified by PCR. After six rounds of positive selection to establish basal binding ability, the murine endothelial cell line, SVEC, was added for negative selection following SELEX. After 16 and 17 cycles, monocyte-targeting ssDNAs were analyzed by next-generation sequencing (NGS) via Illumina MiSeq system. Finally, monocyte specific aptamers were selected by running the SELEX approach for around 20 repeated cycles. The resulting aptamers specific to RAW264.7 (FIG. 1A) and J774A.1 (FIG. 1B) were amplified with PCR. The binding affinity of the resulting aptamers specific to RAW264.7 and J774A.1 was measured by flow cytometry. In brief, $5\times10^5$ of either RAW264.7 or J774A.1 cells were pre-mixed in a blocking buffer (20% FBS and 10% salmon sperm DNA in PBS) at 4° C. for 30 minutes. After that, cells were reacted with increasing serial dilutions of Cy5-labeled aptamer (0 nM to 300 nM) in the blocking buffer at 4° C. for 30 minutes. Unbound Cy5-labeled was removed by washing with 2% FBS in PBS and centrifugation at 300 g for 3 minutes at 4° C. Finally, the sample was subjected to flow cytometry. FIG. 1C shows the biding affinity of the resulting aptamers (AptR) specific to RAW264.7 and FIG. 1D shows the biding affinity of the resulting aptamers (AptR) specific to J774A.1. FIG. 1E shows in vitro monocyte specific aptamer selection using quantitative PCR.

The cell-SELEX processes described above yielded J10 aptamer as the best candidate. The sequence of J10 was then scrambled to yield a control aptamer, S2. The resulting S2 aptamer has the same nucleotide composition as the J10 aptamer but was ordered in different sequence. The sequences of J10 and S2 are provided below in Table 2.

TABLE 2

Aptamer Sequences.

| SEQ. ID NO. | Aptamer | Sequence |
|---|---|---|
| SEQ. ID NO. 4 | J10 | 5'-CAATAGAGTCGTACAGGTCG*ACGCTCG GATGCCACTACAG***GGATGGGAGGGAGGGGG CTCGTGGCGGCTAGGGGGTATAA***CTCATGG ACGTGCTGGTGAC*-3' |
| SEQ. ID NO. 5 | S2 | 5'-CAATAGAGTCGTACAGGTCGTGAGAAG GCGTTGGTCTATCGGGGTCGTGGACTGTCC AAGGGCATGACCGGTCTGACGGTGGCCAGA GACGCAGGAGGGG-3' |

Underlined sequences indicate linker sequences that hybridize with a liposome; italicized sequences indicate the common (primer) sequence in aptamer library which was used for amplification; bolded sequences indicate the binding sequence which can bind to monocyte; sequences in standard font indicate scrambled J10 sequence.

Figure 2A:
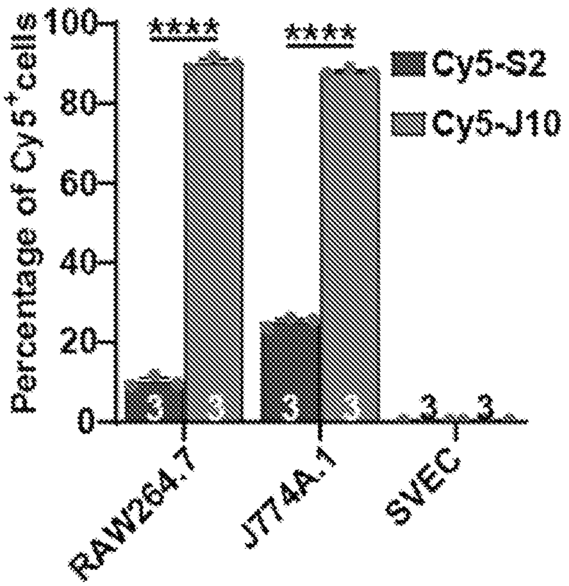
FIGS. 2A-2D include diagrams depicting the specificity of J10 aptamer to monocytes.
Figure 2B:
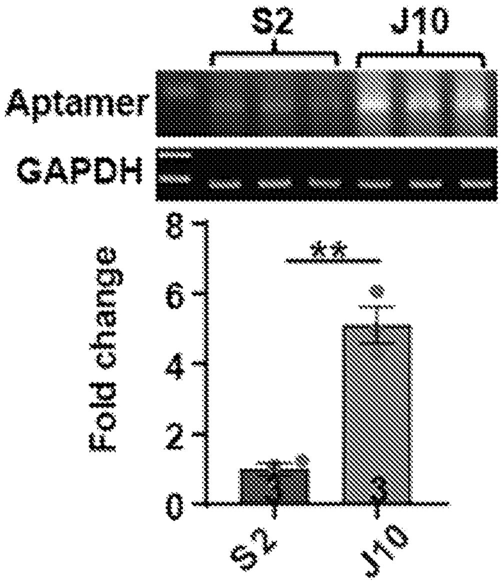

To confirm that J10, but not S2, was capable of binding selectively to monocytes in vitro, the J10 and S2 aptamers were first labeled with the fluorescent labeling reagent Cy5 ((2Z)-2-[(2E,4E)-5-[1-(5-Carboxypentyl)-3,3-dimethyl-5-sulfoindol-1-ium-2-yl]penta-2,4-dienylidene]-1-ethyl-3,3-dimethylindole-5-sulfonate) and then incubated with monocyte cells lines RAW264.7 and J774A.1. Cy5-labeled J10 and S2 were also incubated with the mouse endothelial cell line SVEC which was used as a negative selection. In brief, $5\times10^5$ of each selected cell line was pre-mixed in a bloc king buffer (20% FBS and 10% salmon sperm DNA in PBS) at 4° C. for 30 minutes. After that, the cells were reacted with 200 nM Cy5-J10 or Cy5-S2 in the blocking buffer at 4° C. for 30 minutes. Finally, the sample was subjected to flow cytometry using standard protocols known in the art. As shown in FIG. 2A, the percentage of Cy5-labeled J10 monocytes (RAW264.7 and J774A.1 cells) was significantly higher than the percentage of Cy5-labeled S2 monocytes and there was no detection of either Cy5-labeled J10 or Cy5-labeled S2 in the endothelial mouse cell line SVEC. Also, PCR analysis confirmed in vivo targeting ability of J10 aptamer to the injured site following intravenous injection of Cy5-labeled J10 or S2 in the mouse cardiac ischemia reperfusion (I/R) model (FIG. 2B). Together, the data in FIGS. 2A and 2B confirmed that J10, but not S2, was capable of binding selectively to monocytes in vitro and being carried to the injured site in vivo.

Figure 2C:
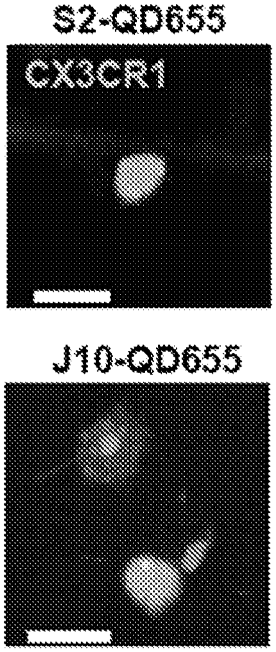

To confirm that J10, but not S2, was also capable of binding selectively to monocytes in vivo, aptamer-quantum dot conjugates were first formed by modifying quantum dot (QD) nanoparticles fluorescing at 655 nm (QD655, Invitrogen) with either J10 or S2 aptamers. The QD655s modified with S2 or J10 were then used to visualize J10-QD655s tagged monocytes passing through a mouse blood vessel in vivo via multi-photon intravital imaging. Multi-photon intravital imaging was performed in a manner similar to a procedure described in Vinegoni et al., *Nat. Protoc.* 10, 1802-1819 (2015). In brief, male 10-12 week old heterozygous transgenic mice B6.129P2(Cg)-Cx3cr1$^{tm1Litt}$/J (CX3CR1$^{GFP/WT}$), obtained from the Jackson Laboratory, USA, were used for intravital imaging. All animals were anesthetized by 1.5% isoflurane (Minrad) during the experiment. Twenty L of QD655s modified with either J10 or S2 aptamers were then injected to CX3CR1$^{GFP/WT}$ mice for an hour, and the area of interest was visualized by multi-photon microscope (FVMPE-RS, Olympus) following excitement of the injected QD655 probe. As shown in FIG. 2C, intravital imaging detected in vivo targeting of J10 aptamer-QD655s, but not the S2 aptamer-QD655s, to circulating CX3CR1-GFP$^{+}$ monocytes. The data in FIG. 2C confirmed that J10, but not S2, was capable of binding selectively to monocytes in vivo.

Figure 3:
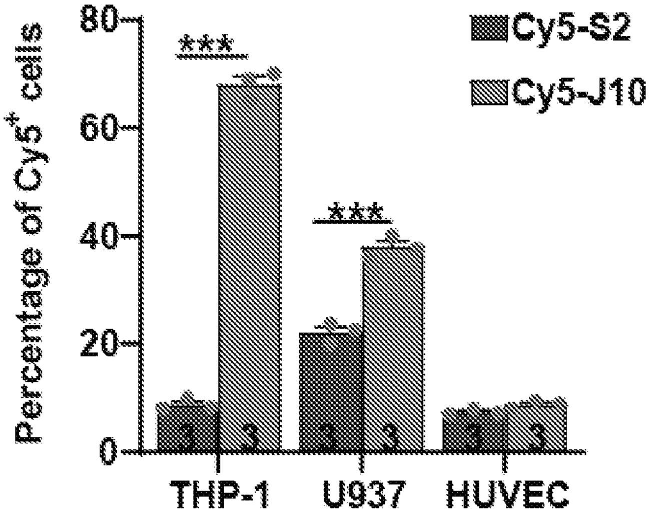
FIG. 3 depicts a graph showing the affinity of the J10 aptamer against the human monocyte cell lines THP-1 and U937, as measured by flow cytometry. The aptamers were labelled with Cy5 dye. The S2 aptamer had the same nucleotide composition as J10 aptamer but in a random sequence. The S2 aptamer was used as a control. The human umbilical cord endothelial cells (HUVEC) were used as a negative control. The two-way ANOVA with a Tukey adjustment was used to analyze the data. $***P>0.001$.

To confirm that J10 binding, but not S2 binding, was selective to human monocytes in vitro, Cy5-labeled J10 and S2 were also incubated with the human monocyte cell lines, THP-1 and U937, and human umbilical cord endothelial cells (HUVEC), which were used as a negative control. In brief, $5\times10^5$ of each selected cell line was pre-mixed in a bloc king buffer (20% FBS and 10% salmon sperm DNA in PBS) at 4° C. for 30 minutes. After that, the cells were reacted with 200 nM Cy5-J10 or Cy5-S2 in the blocking buffer at 4° C. for 30 minutes. Finally, the sample was subjected to flow cytometry using standard protocols known in the art. As shown in FIG. 3, the J10 aptamer was also shown to have a high binding affinity towards human monocyte cell lines THP-1 and U937, but not human endothelial cell line HUVEC, whereas S2 had no binding affinity in any of the cell lines tested.

Figure 2D:
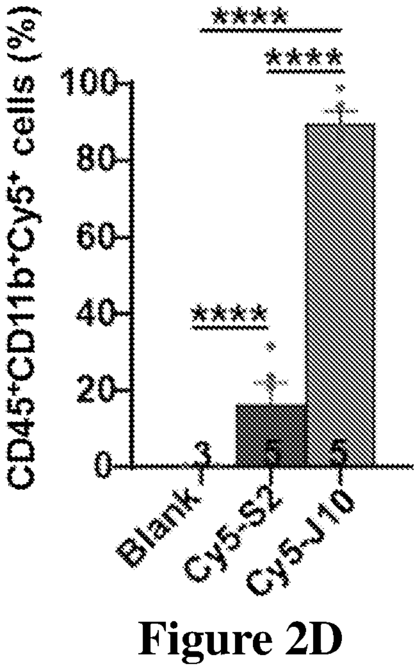

To test for ex vivo binding specificity and affinity, 100 μL peripheral blood from healthy mice was withdrawn via the submandibular vein, collected in EDTA-containing anticoagulant tubes (BD Vacutainer), and incubated with 2 mL ACK lysing buffer for 10 minutes to lyse the red blood cells. After that, 2% FBS in PBS was added to stop the reaction. Following centrifugation (300 g for 3 minutes at 4° C.) the supernatants were removed. One million cells were blocked by CD16/CD32 Fc blocking antibody (1:100; Invitrogen) after incubation for 20 minutes. Then the cells were stained for CD45 (PE-Cy7; 1:100; Biolegend), CD11b (PE; 1:200; Biolegend) and 2 μM Cy5-Apt for 30 minutes at 4° C. Finally, the cells were washed by 2% FBS in PBS and subjected to flow cytometry using standard protocols known in the art. As shown in FIG. 2D, the J10 aptamer possessed high affinity to circulating myeloid cells (CD45$^{+}$ CD11b$^{+}$ cells).

Together, the data provided in Example 1 demonstrate that the J10 aptamer, identified by the cell-SELEX method, can selectively bind to both murine and human circulating monocytes with good affinity.

Example 2. Formation of an Aptamer-Based Lipid Nanoparticle Targeting System Synthesis and Purification of Linker-PEG-DSPE Conjugates. TCEP (tris(2-carboxyethyl) phosphine) (1.5 mM, pH=7.0) was incubated with disulfide-labelled DNA (molar ratio=100:1) overnight at 4° C. Linker-DNA was precipitated using 3-fold cold ethanol and 0.1-fold cold sodium acetate (3 M) at −80° C. for 30 minutes followed by subsequent centrifugation at 17,000 rpm. Linker-DNA was then conjugated with 1,2-distearoyl-sn-glycero-3-phosphoethanolamine-N-[maleimide(polyethylene glycol)-2000] (Mal-PEG-DSPE, Avanti) by incubation with TCEP (molar ratio for linker-DNA:TCEP:Mal-PEG-DSPE=1:10:20) overnight at 4° C. and dried through lyophilisation. Finally, high performance liquid chromatography (HPLC) was used to purify linker-lipid and remove free linker-SH and free Mal-lipid in acetonitrile (ACN) and triethylammonium acetate (TEAA) system. Mobile phase was started from 20% ACN to 100% ACN in 40 minutes at 1 mL/min flow rate with C5 column (Sigma).

Manufacture of Lipid Nanoparticles and Loading Thereof Lipid nanoparticles (LNPs) were synthesized by using thiolated linker that readily attached to maleimide-containing DSPE-PEG. Specifically, lipid film (total mass=35 mg) was prepared in a round-bottom flask by dissolving DSPC, cholesterol and DSPE-PEG in chloroform and DSPE-PEG-linker and DiD in methanol (molar ratio=45:50:0.047:0.003:0.005). Solvent was removed under reduced pressure at room temperature and the lipid film was lyophilised overnight.

After lyophilizing the lipid film, the dry film was hydrated with 1 mL internal buffer (100 mM or 200 mM calcium acetate) to form multi-layer vehicles (MLV). After the thin film was completely dissolved, the size of MLV was reduced by 10 freeze-thaw cycles under vacuum using liquid nitrogen and 65° C. water bath. It was then sonicated using probe sonicator in total for 2 minutes through a series of 2 seconds sonication and 10 seconds pause. Following this, MLV was extruded through a 0.1 μm polycarbonate membrane for 21 times at 65° C. to obtain around 100 nm single-layer vehicles (SLV)-linker-LNP.

A therapeutic of interest was added for loading into the LNPs. In an exemplary method, IOX2, a potent inhibitor of HIF-1α prolyl hydroxylase-2 (PHD2), was used as the therapeutic of interest. The active loading method for IOX2 encapsulation was optimized to determine the best external buffer and drug-to-lipid ratio for encapsulation efficiency. In brief, the internal buffer was replaced with external buffer. Then, IOX2 was encapsulated with a drug to lipid molar ratio of 0.1, 0.2, or 0.4 at 65° C. for 30 minutes. Following this, the external buffer was replaced with PBS to remove non-encapsulated IOX2. Results were compared to a controlled experiment where the both the internal and external buffer were 150 mM NaCl.

Conjugation of Lipid Nanoparticles with Aptamers. In an exemplary method, linker-IOX2-LNPs were conjugated with J10 and S2 aptamers separately through overnight incubation at room temperature (linker:aptamer=1:2.5) followed by purification using sepharose CL-4B size exclusion column with PBS as the mobile phase. The efficient ratio of linker and aptamer for aptamer-liposomes fabrication was measured as a percentage of hybridization efficiency using the following equation:

$$\text{Hybridization efficiency (\%)} = \frac{\text{reacted aptamer}}{\text{linker on the liposome}} \times 100\%.$$

Several linker to aptamer ratios were tested to identify the optimal amounts as shown in Table 3.

TABLE 3

Efficient ratio of linker and aptamer for aptamer-liposomes fabrication.

| Aptamer | Linker to aptamer ratio | Aptamer Added (pmol) | Unreacted Aptamer (pmol) | Reacted Aptamer (pmol) | Hybridization efficiency (%) |
|---|---|---|---|---|---|
| J10 | 1:0.25 | 100 | 37 | 63 | 9.2 |
| J10 | 1:0.5 | 200 | 79 | 121 | 19.9 |
| J10 | 1:1.25 | 500 | 190 | 310 | 47.6 |
| J10 | 1:2.5 | 1000 | 328 | 672 | 82.0 |
| J10 | 1:5 | 2000 | 331 | 1669 | 82.7 |
| S2 | 1:2.5 | 1000 | 316 | 684 | 78.9 |

Figure 4A:
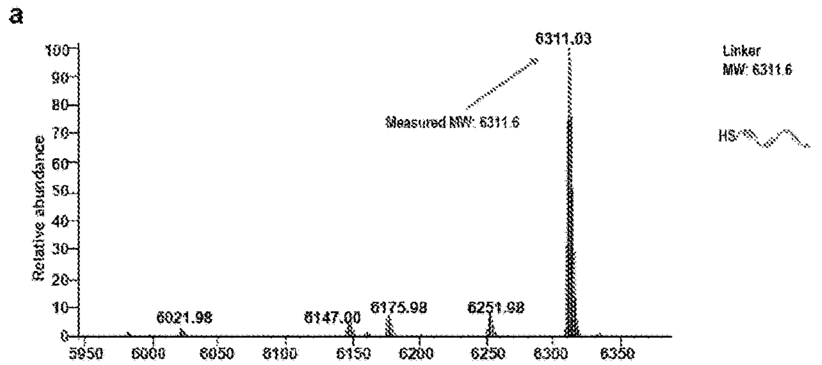
FIGS. 4A-4C depict images of mass spectra of lipid nanoparticles (LNPs).
Figure 4B:
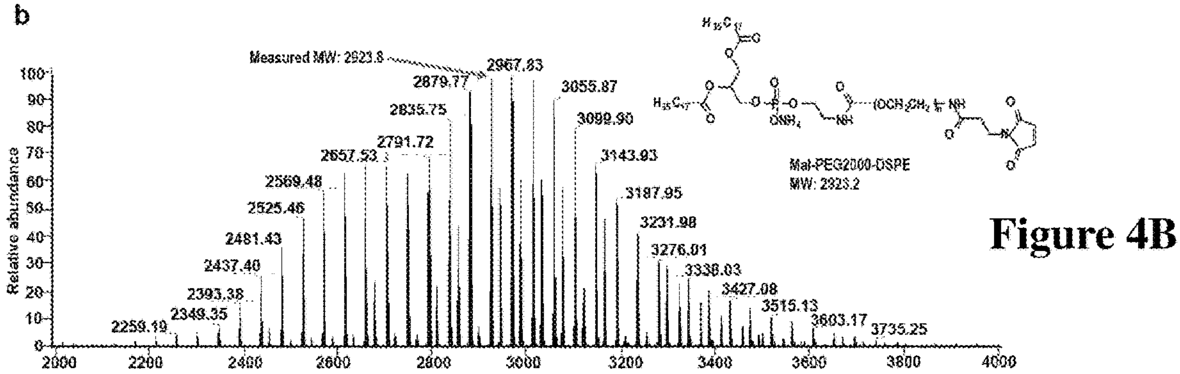
Figure 4C:
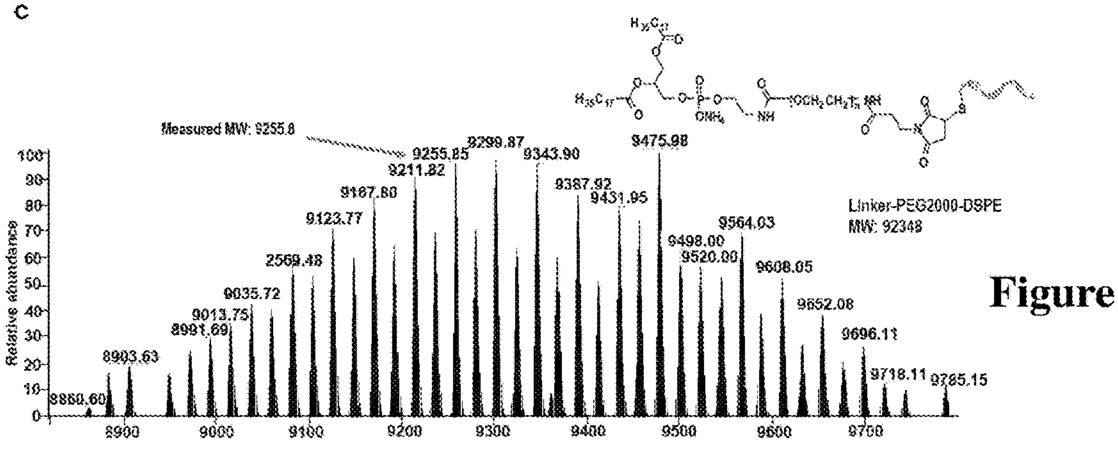

Mass spectrometry measurement was performed after each step to confirm the success of the synthesis using standard protocols known in the field (FIGS. 4A-4C).

Figure 5A:
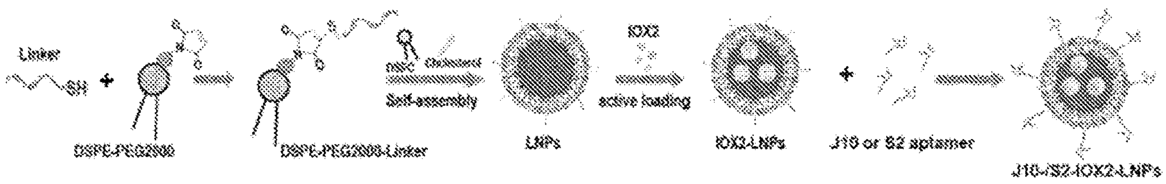
FIGS. 5A-5H include diagrams depicting J10 aptamer-conjugated IOX2-lipid nanoparticles (LNPs) targeted to circulating monocytes.
Figure 5B:
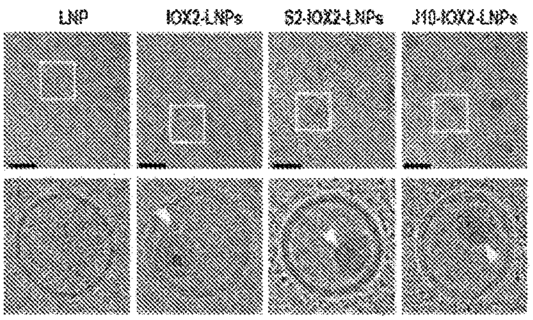

Cryogenic electron microscopy was performed to visualize the lipid nanoparticles. Briefly, the holey carbon film-covered 200-mesh copper grids (Electron Microscopy Sciences) were glow-discharged for 15 seconds on the carbon side. Samples (4 μL) containing 15 μM lipid concentration were pipetted onto the grids followed by blotting in 100% humidity at 4° C. for 3 seconds and plunge-frozen into liquid ethane cooled by liquid nitrogen using a Vitrobot (Thermo Fisher Scientific). Grids were stored under liquid nitrogen and transferred to the electron microscope using a cryostage. Images of liposomes within the holes in the carbon film were obtained by using a Tecnai F20 electron microscope (Thermo Fisher Scientific) at 200 keV with a 70 μm objective aperture. The low dose condition for each exposure was ~25 $e^-/Å^2$. Images were taken at 2 μm defocus and recorded on 4k×4k CCD camera (Gatan, USA). Cryogenic electron microscopy confirmed successful encapsulation of IOX2 (FIG. 5B).

Figure 5C:
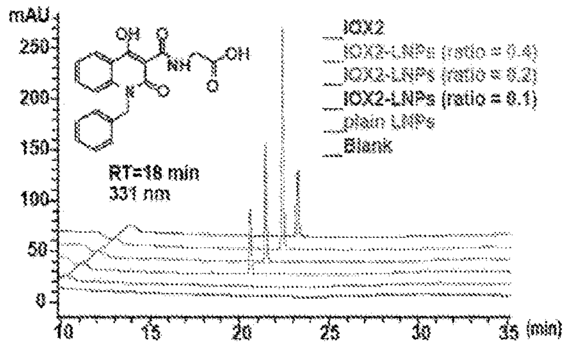

HPLC analysis was also performed on the lipid nanoparticles. Briefly, lipid nanoparticles (with initial drug to lipid concentrations at ratios of 0.1, 0.2, or 0.4) were dissolved in $ACN/H_2O$ (20:80) for measurement. Separation was carried out with a Waters e2695 separation module using $ACN/H_2O$ (from 20:80 to 100:0) at a flow rate of 1 mL/minute in an X-Bridge C18 column in 40 min at room temperature. Detection was performed using a Waters 2489 UV/Vis detector 20 at 331 nm. HPLC analysis confirmed successful encapsulation of IOX2 (FIG. 5C).

LNPs with and without aptamers were then characterized for size and zeta potential measurement. All sizing and zeta potential measurements were made on a Zetasizer Nano ZS at 25° C. Sizing measurements were made on the neat liposome samples, whereas the samples were diluted 1 in 10 with PBS for the zeta potential measurements. In an exemplary example, size and zeta potential measurements were collected for IOX2-carrying LNPs with and without the J10 aptamer. As shown in Table 4, attachment of aptamer increased the size and the negativity of the zeta potential.

TABLE 4

Size and zeta potential of IOX2 encapsulated aptamer-liposomes.

| | Size (Z-average (d · nm)) | Polydispersity Index (PDI) | Zeta Potential (mV) |
|---|---|---|---|
| IOX2-LNP | 96.2 ± 0.6 | 0.146 ± 0.002 | −3.37 ± 0.43 |
| Linker-IOX2-LNP | 108.9 ± 1.2 | 0.149 ± 0.008 | −27.70 ± 1.33 |
| J10-IOX2-LNP | 122.8 ± 3.1 | 0.121 ± 0.012 | −30.40 ± 2.09 |

Figure 5D:
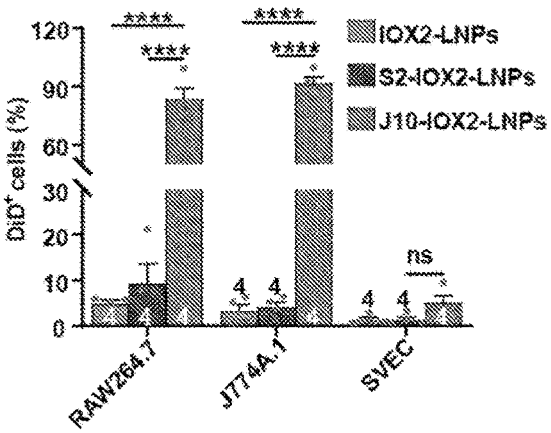

Characterization of Specificity Lipid Nanoparticles with Aptamers. In vitro binding affinity of aptamer-IOX2-LNPs to mouse monocyte cell lines J774A.1 and RAW264.7 and mouse endothelial cell line SVEC was measured. Briefly, $5\times10^5$ of each selected cell line was pre-mixed in a blocking buffer (20% FBS and 10% salmon sperm DNA in PBS) at 4° C. for 30 minutes. After that, the cells were reacted with 5 μM J10-IOX2-LNP, S2-IOX2-LNP, or IOX2-LNP in the blocking buffer at 4° C. for 30 minutes. Unbound aptamer-IOX2-LNP was removed by washing with 2% FBS in PBS and centrifugation at 300 g for 3 minutes at 4° C. Finally, the sample was subjected to flow cytometry. As shown in FIG. 5D, J10-decorated LNPs were able to bind to monocytes more effectively compared to S2- and non-decorated LNPs, with minimal binding to endothelial cells.

Example 3. Circulating Monocytes are Increased and Recruited to Injured Heart Following Cardiac Ischemia Reperfusion In order to determine the most efficient time point for the delivery of therapeutics for the treatment of both cardiac ischemia reperfusion (I/R), monocyte recruitment profiles were constructed using I/R models of male 6-8 week old heterozygous transgenic mice B6.129(Cg)-Ccr2$^{tm2.1Ifc}$/J (CCR2$^{RFP/WT}$) obtained from the Jackson Laboratory, USA.

To generate the murine I/R models, 8-10 weeks old mice were anesthetised with 80 mg/kg Zoletil 50 and 3.5 mg/kg Rompun and given $O_2$ via a tracheal tube on the 37° C. heating pad. The heart was accessed via left thoracotomy between the third and fourth ribs. The left anterior descending coronary artery was temporarily ligated with sutures 7-0 polypropylene through polyethylene-10 tubing for 45 minutes. Subsequently, polyethylene-10 tubing was removed to induce myocardial ischemia/reperfusion injury. The success of the surgery was evaluated by echocardiography on the following day.

Figure 6:
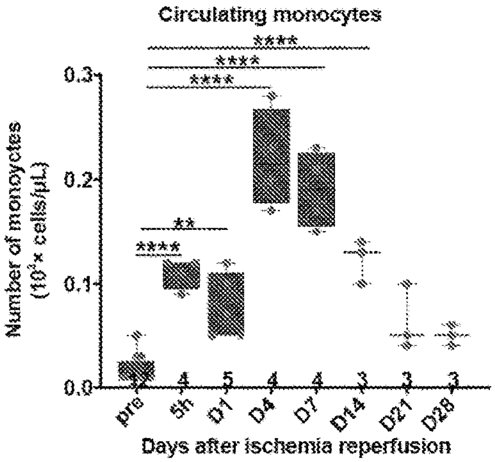
FIG. 6 depicts a graph showing the increased number of circulating monocytes in a mouse after cardiac ischemia reperfusion was determined with complete blood count (CBC) at 5 hour (5 h) and on Day 1, 4, 7, 14, 21 and 28. The one-way ANOVA with a Tukey adjustment was used for data analysis where $P>0.01$; $**P>0.0001$ were significant.

The number of circulating monocytes after cardiac ischemia reperfusion was determined with complete blood count (CBC) at 5 hour (5 h) and on Day 1, 4, 7, 14, 21 and 28. Data showed an increase in the number of circulating RFP$^+$ monocytes following I/R injury that reached maxim amounts at day 4 post I/R injury (FIG. 6).

Figure 7A:
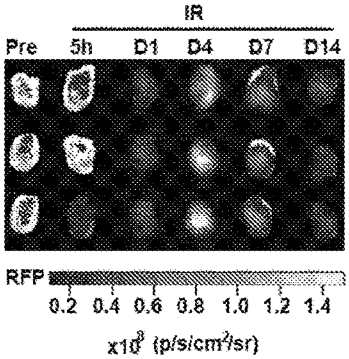
FIGS. 7A-7C depict images of CCR2-RFP$^+$ cell recruitment to injured heart after ischemia/reperfusion (I/R) via in vivo imaging system (IVIS) imaging.
Figure 7B:
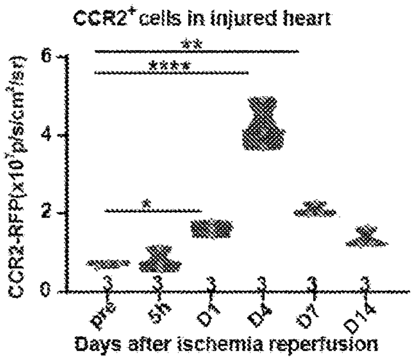
Figure 7C:
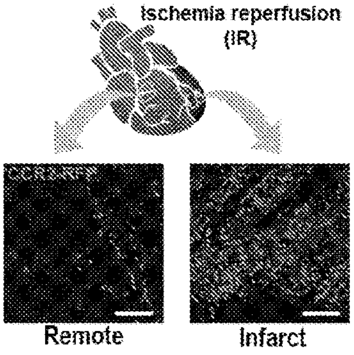

Transplantation success and recruitment of monocytes were confirmed by in vivo imaging system (IVIS) imaging. Analysis of circulating monocytes by complete blood count was carried out using blood samples collected from WT mice at certain time points following the I/R surgery. Analysis of monocyte recruitment to the heart was performed by in vivo imaging system (IVIS) imaging using hearts harvested from CCR2$^{RFP/WT}$ mice at certain time points following I/R surgery through the quantification of RFP fluorescent signal. IVIS imaging revealed CCR2-RFP$^+$ cell recruitment to injured heart after I/R (FIGS. 7A and 7B) whereby CCR2-RFP$^+$ monocytes were clearly observed at the injection site (FIG. 7C).

Example 4. Therapeutic Use of Drug-Loaded Lipid Nanoparticles

Figure 5E:
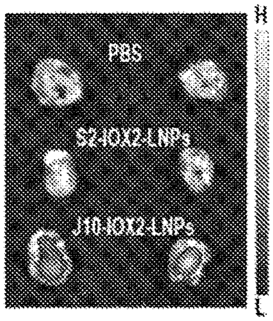
Figure 5F:
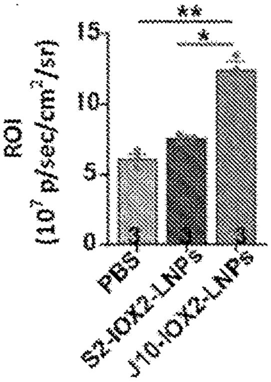
Figure 5G:
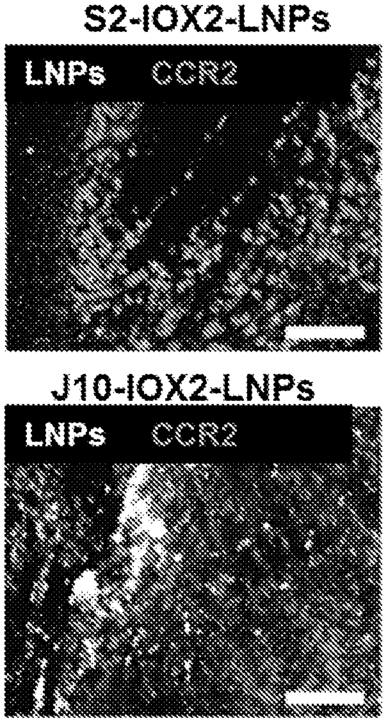

Recruitment of IOX2-loaded nanoparticles to the injured heart was assessed by in vivo imaging system (IVIS) imaging. Briefly, multi-photon intravital imaging was performed in a manner similar to a procedure described in Vinegoni et al., *Nat. Protoc.* 10, 1802-1819 (2015). All animals were anesthetized by 1.5% isoflurane (Minrad) during the experiment. S2-IOX2-LNP and J10-IOX2-LNP particles were first labelled with DiD lipophilic cyanine dyes and then 5 mM 100 μL S2-IOX2-LNP and J10-IOX2-LNP were injected to I/R day 1 CCR2$^{RFP/WT}$ mice. One hour after injection, then the infarct area was visualized by fluorescence of the DiD-labelled particles using a by multi-photon microscope (FVMPE-RS, Olympus). IVIS analysis (FIGS. 5E and 5F) showed a significant increase of fluorescence for J10-IOX2-LNPs compared to PBS (background) and S2-IOX2-LNPs, indicative of the success of J10-decorated nanoparticles to target the heart following I/R injury. Accumulation of aptamer-IOX2-LNPs was observed the infarct area under an intravital microscope during IVIS analysis which further confirmed the attachment of J10-LNPs to CCR2-RFP$^+$ monocytes in vivo (FIG. 5G).

Figure 5H:
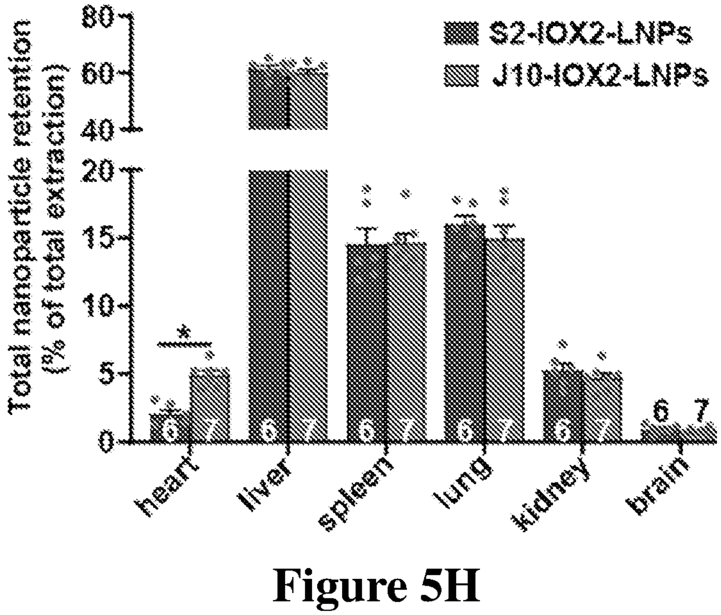

To determine the biodistribution of aptamer-IOX2 LNPs, systemic perfusion was performed and organs were harvested and weighed 4 hours following one dose administration of PBS, S2-IOX2-LNP or J10-IOX2-LNP to IR-5 h mice. Organs were homogenized in 500 μL ACN using MagNa Lyser (Roche) for 10 times at maximum speed for 30 seconds each time. Samples were then sonicated for 2 minutes (5 times) and centrifuged at 18,800 g for 30 minutes at 4° C. Supernatant was then collected and IOX2 amount was quantified by HPLC (Waters e2695 separation module) using an X-Bridge C10 column at 25° C. Gradient elution was performed from ACN/$H_2O$ (20:80) to ACN/$H_2O$ (100:0) in 20 minutes at 1 mL/min flow rate. Detection was performed using a Waters 2489 UV/Vis detector at 331 nm. As shown in FIG. 5H, the biodistribution study of IOX2-loaded S2- and J10-LNPs demonstrated a significant increase of IOX2 retention in the heart for J10-LNPs, indicating that an aptamer-based lipid nanoparticle targeting system can increase drug deliverability to the heart.

Figure 8A:
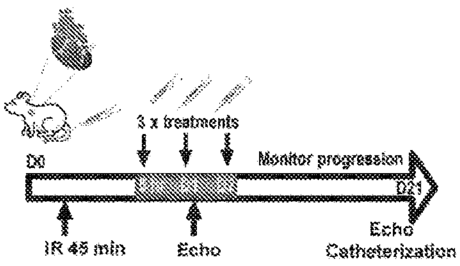
FIGS. 8A-8P include diagrams depicting improved heart functions after ischemia reperfusion (IR) following treatment with J10 aptamer-IOX2-LNPs.
Figure 8B:
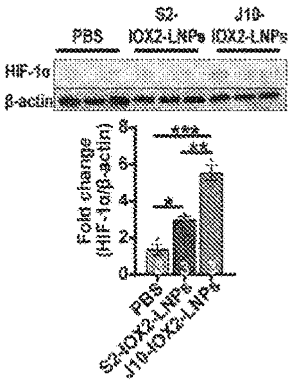
FIG. 8B: depicts images of the protein levels of HIFla after aptamer-IOX2-

The therapeutic effect of the IOX2-loaded nanoparticles was then examined in a murine model of myocardial I/R injury (FIG. 8A). To assess expression of hypoxia-inducible factor 1-alpha (HIF1α, hearts were harvested 24 hours following an administration of PBS, S2-IOX2-LNP or J10-IOX2-LNP to I/R 5 h mice. Samples were treated with 300 μL RIPA buffer containing protease inhibitor cocktail (Thermo), homogenised by MagNa Lyser twice at maximum speed for 20 s each time and suspended by centrifugation (18,800 g, 30 minutes, 4° C.). Supernatant was collected and mixed with 6× protein loading dye and heated for at 100° C. for 10 minutes. 8% SDS page were used in electrophoresis and proteins were stained by anti-HIF-1α antibody (1:1000, Cell Signaling) and anti-3-actin antibody (1:5000; Merck). Western blot analysis showed increased expression of hypoxia-inducible factor 1-alpha (HIF1α (FIG. 8B).

Figure 8C:
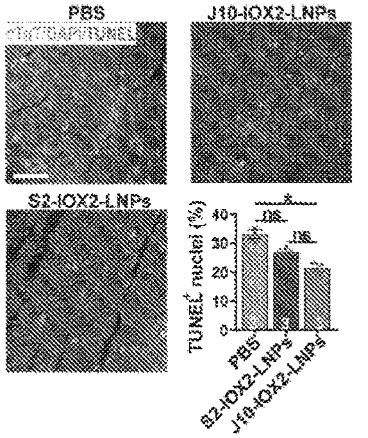
FIG. 8C: depicts images of terminal deoxynucleotidyl transferase (TdT) dUTP nick-end labeling (TUNEL) analysis for detection of apoptosis in the injured heart after aptamer-IOX2-LNPs treatment. The apoptotic index was defined as of the percentage of $TUNEL^+$ cells in a field examined.

To examine myocardial apoptosis, a TUNEL assay was performed. First, hearts were harvested 24 hours after the administration of PBS, S2-IOX2-LNP or J10-IOX2-LNP to I/R-5 h mice. Hearts then were fixed in 4% w/v paraformaldehyde (PFA) in PBS overnight and embedded in paraffin and sectioned. Slides were treated with xylene to remove paraffin and down-gradient ethanol to rehydrate. Next slides were processed using ApopTag® Red In Situ Apoptosis Detection Kit (Millipore) according to the manufacturer's protocol. Slides were also stained by troponin I (1:100; Abcam) and DAPI (1:1000; Sigma) in PBS containing 10% FBS/goat serum at 4° C. overnight. Then, slides were washed by PBS three times and were stained by secondary antibody goat anti-rabbit IgG-AlexaFluor 488. Images were captured by Pannoramic 250 FLASH II and quantified by CaseViwer 2.0. The TUNEL assay revealed significant decrease in apoptotic cells in J10-IOX-LNPs group, indicating the success of our treatment in preventing cardiac cell death (FIG. 8C).

Figure 8D:
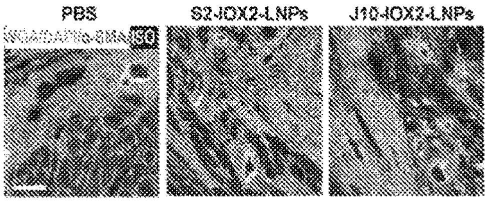
FIGS. 8D-8F depict images showing angiogenesis markers in the injured mouse heart after aptamer-IOX2-LNPs treatment.
Figure 8E:
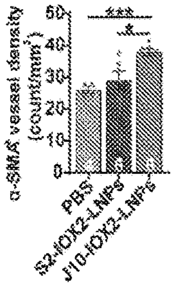
Figure 8F:
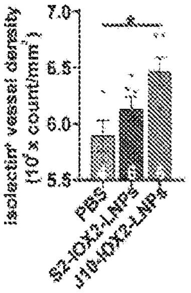

For angiogenesis measurement, hearts were harvested at day 21 after the administration of PBS, S2-IOX2-LNP or J10-IOX2-LNP after I/R 5 h, 24 h and 48 h. Hearts then were fixed in 4% w/v paraformaldehyde (PFA) in PBS overnight and embedded in paraffin and sectioned. Slides were treated with xylene to remove paraffin and down-gradient ethanol to rehydrate. Slides were then stained by alpha-smooth muscle actin (α-SMA; 1:400; Sigma), isolectin (1:400; Invitrogen), wheat germ agglutinin (WGA, 1:100; Invitrogen), and DAPI (1:1000; Sigma) using protocols standard in the art. Vessels including arteries, veins and arterioles were stained by α-SMA. Capillaries were stained with isolectin, indicating endothelial cells. Cardiomyocytes were visualised by WGA. Images were captured by Pannoramic 250 FLASH II and quantified by CaseViwer 2.0. The increased amount of α-SMA- and isolectin-positive vessels observed in the J10-IOX2-LNP-treated I/R mouse model indicated the success of J10-IOX2-LNPs in promoting angiogenesis (FIGS. 8D-8F).

Figure 8G:
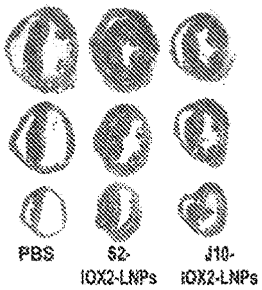
FIGS. 8G and 8H depict images of heart sections stained using the Masson's trichrome stain method to detect the effects of aptamer-IOX2-LNPs on cardiac fibrosis on day twenty-one after IR in the mouse (FIG. 8G) and graphs quantifying the observed cardiac fibrosis after aptamer-IOX2-LNPs treatment (FIG. 8H).
Figure 8H:
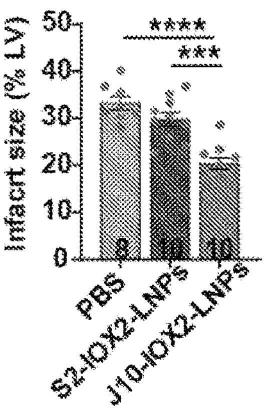
Figure 8I:
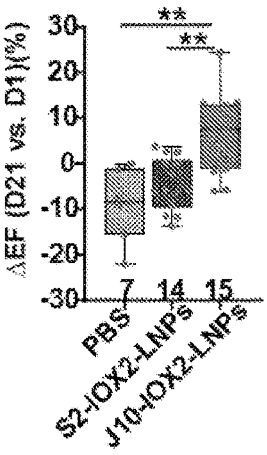
Figure 8J:
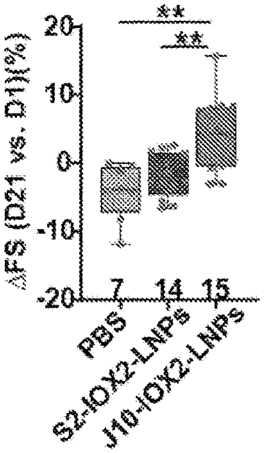
Figure 8K:
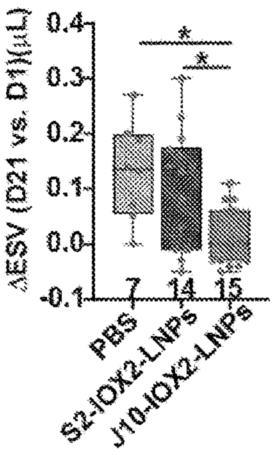
Figure 8L:
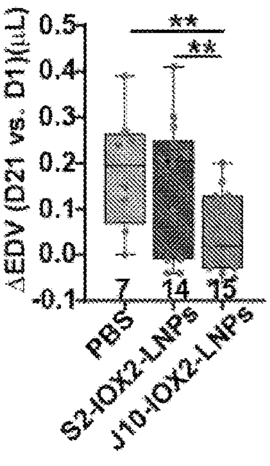
Figure 8M:
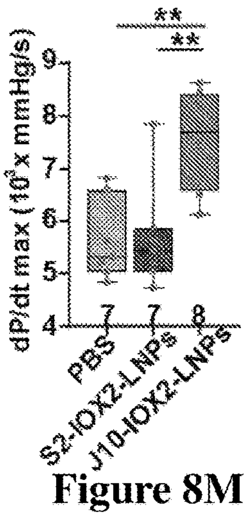
Figure 8N:
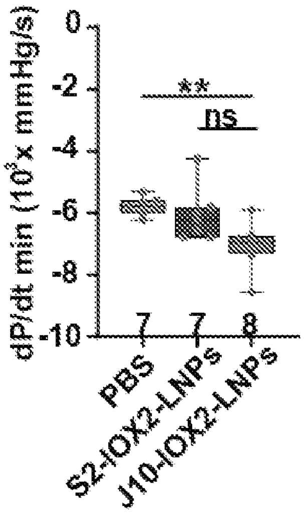
Figure 8O:
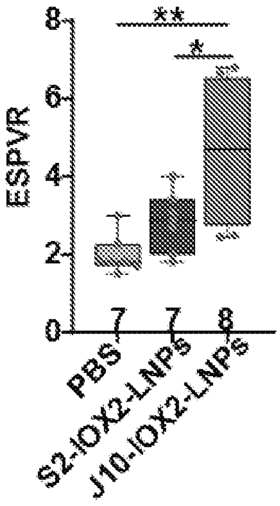
Figure 8P:
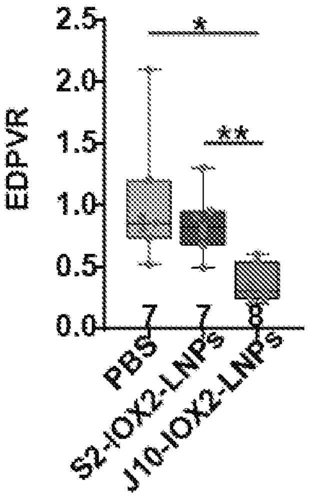
Figure 9A:
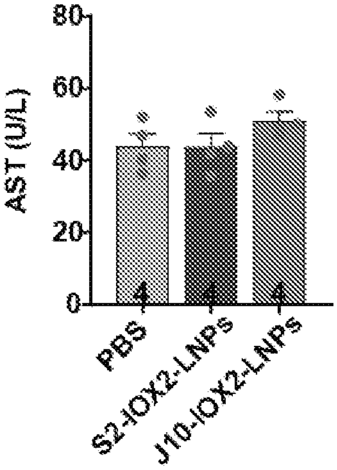
FIGS. 9A-9E depict graphs showing the effects of aptamer-IOX2-LNPs on the liver and kidney function were examined through blood test one week after particle injection in a mouse. One-way ANOVA with a Tukey adjustment was used for data analysis.
Figure 9B:
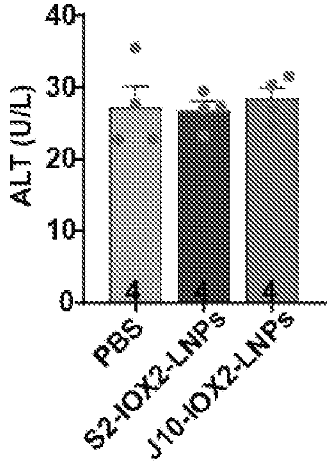
Figure 9C:
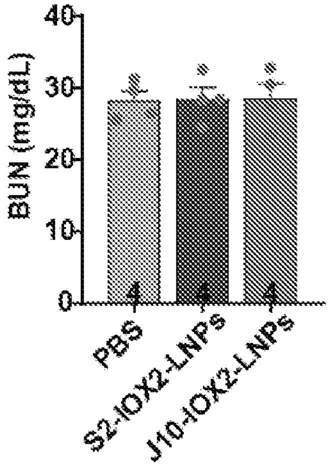
Figure 9D:
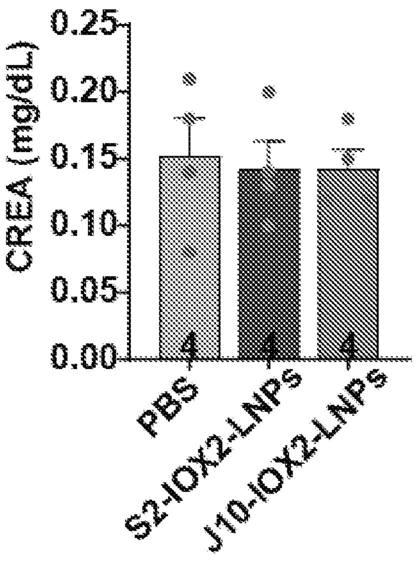
Figure 9E:
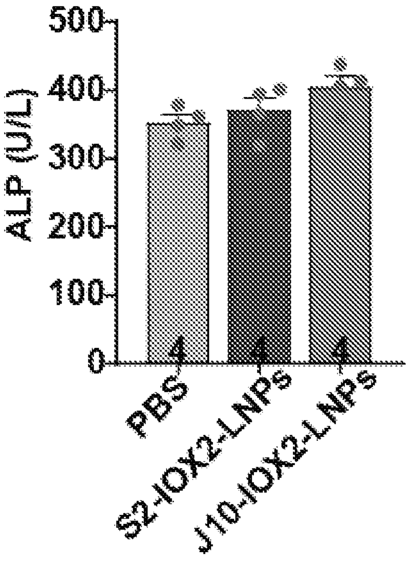

For cardiac fibrosis measurement, hearts were harvested at day 21 after the administration of PBS, S2-IOX2-LNP or J10-IOX2-LNP after I/R 5 h, 24 h and 48 h. Hearts then were fixed in 4% w/v paraformaldehyde (PFA) in PBS overnight and embedded in paraffin and sectioned. Slides were treated with xylene to remove paraffin and down-gradient ethanol to rehydrate. Fibrosis was then assessed by the Masson's trichrome stain method (Masson trichrome kit, Sigma) performed according to the manufacturer's protocol. Images were captured by Pannoramic 250 FLASH II and quantified by ImageJ software. Quantification of cardiac fibrosis at day 21, by trichrome staining of three layers of the heart, showed that the J10-IOX2-LNP-treated group had a significant reduction of infarct size compared to the controls (FIGS. 8G and 8H).

The cardiac function of the mice from each group was also examined at day 21 by echocardiography and cardiac catheterization. Echocardiography was used to measure the cardiac function of I/R mice by Vivid-q Ultrasound (GE) equipment and 13.0 MHz intraoperative probe. Mice were anesthetised by 0.5-1% isoflurane and heart rate was maintained approximately 450±50 beats per min (bpm) for further measurement. The images of parasternal short axis and parasternal long axis were captured by 2D B-mode imaging for monitoring the papillary muscles and septal wall in left ventricle and a small segment of right ventricular wall. Subsequently, 1D M-mode revealed cardiac dimensions and contractility. The parameters of cardiac function were revealed by ejection fraction (EF), fractional shortening (FS), end-diastolic volume (EDV) and end-systolic volume (ESV). Cardiac catheterization was also measured in the mice following a procedure similar to that of Pacher et al., *Nat. Protoc.* 3, 1422-1434 (2008). In brief, mice were anesthetized by urethane (1 mg/g) and given $O_2$ via a tracheal tube on a 37° C. heating pad. The Millar SPR-839 Pressure-Volume (PV) catheter was put into the left ventricle (LV) along the right carotid to avoid opening chest cavity. The parameters of cardiac systolic and diastolic dysfunction were revealed by the peak rate of pressure ascended ($dP/dt_{max}$), end-systolic pressure-volume relation (ESPVR), peak rate of pressure declined ($dP/dt_{min}$) and end-diastolic pressure-volume relationship (EDPVR). All measurements were performed using LabChart Pro analysis software. The J10-IOX2-LNP-treated group of I/R injured mice showed significant improvement in all of the measured cardiac parameters in comparison to S2-IOX2-LNP-treated group and PBS-treated group of I/R injured mice (FIGS. 8I-8P).

Biosafety analysis of J10-IOX2-LNPs in vivo was carried out in order to examine the effects of J10-IOX2-LNP-treatment on liver and kidney function in I/R injured mice. In brief, peripheral blood was collected 7 days treatment through the submandibular vein and allowed to clot for 15 minutes. Serum was collected for nephrotoxicity and hepatotoxicity assessment by biochemical tests. AST (Aspartate transaminase), ALT (Alanine transaminase) and ALP (Alkaline phosphatase) were measured for liver function and BUN (Blood urea nitrogen) and CREA (Creatinine) were measured for kidney function assessments. The results showed that the nanoparticles were safe and did not cause any significant change in liver and kidney functions (FIGS. 9A-9E).

Figure 10:
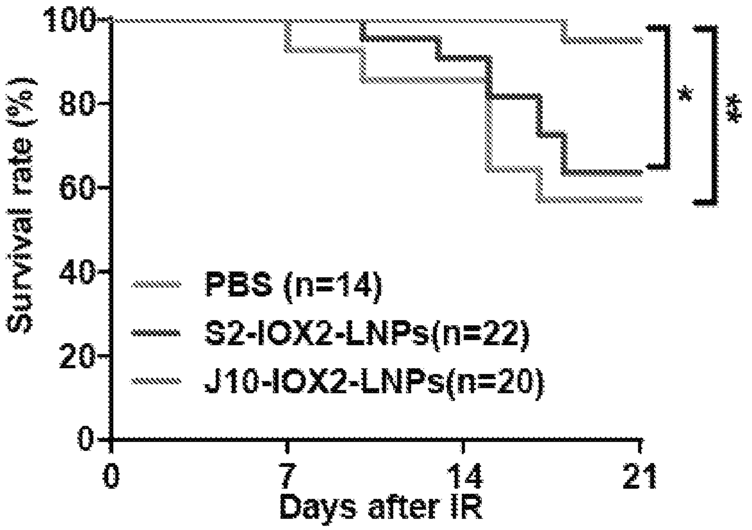
FIG. 10 depicts a graph showing the effects of aptamer-IOX2-LNPs on the survival rate in the mouse cardiac IR model. One-way ANOVA with a Tukey adjustment was used for data analysis and the Kaplan-Meier method and the log-rank (Mantel-Cox) test were used for construction and analysis of the survival curves in q. *$P<0.05$; $P<0.01$; *$P<0.001$; ****$P<0.0001$; ns, not significant.

All of these results combined showed that in the murine model of myocardial I/R injury, our nanoparticles successfully targeted the heart, improved its functions, reduced the infarct size and overall, prolonged the survival of the mice (FIG. 10).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of examples only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A lipid nanoparticle capable of delivering an agent to a heart site, comprising a nucleic acid aptamer, and an agent capable of treating or diagnosing a heart injury, wherein the nucleic acid aptamer is attached to the lipid nanoparticle and the agent is encapsulated by the lipid nanoparticle, and wherein the nucleic acid aptamer comprises a core nucleotide sequence at least 85% identical to 5'-GGA TGG GAG GGA GGG GGC TCG TGG CGG CTA GGG GGT ATA A-3' (SEQ ID NO:1).

2. The lipid nanoparticle of claim 1, wherein the aptamer comprises the core nucleotide set forth by SEQ ID NO:1.

3. The lipid nanoparticle of claim 1, wherein the aptamer comprises a 5' primer site and 3' primer site flanking the core nucleotide sequence.

4. The lipid nanoparticle of claim 3, wherein the 5' primer site is set forth by the sequence 5'-AC GCT CGG ATG CCA CTA CAG-3' (SEQ ID NO. 3), and/or wherein the 3' primer site is set forth by the sequence 5'-CT CAT GGA CGT GCT GGT GAC-3' (SEQ ID NO. 6).

5. The lipid nanoparticle of claim 4, wherein the aptamer is set forth by the sequence 5'-AC GCT CGG ATG CCA CTA CAG GGA TGG GAG GGA GGG GGC TCG TGG CGG CTA GGG GGT ATA ACT CAT GGA CGT GCT GGT GAC-3' (SEQ ID NO: 2).

6. The lipid nanoparticle of any one of claims 1-5, wherein the aptamer is conjugated to an anchor nucleic acid fragment.

7. The lipid nanoparticle of claim 6, wherein the anchor nucleic acid fragment is set forth by the sequence 5'-CAA TAG AGT CGT ACA GGT CG-3' (SEQ ID NO: 7), which optionally is located at the 5' end of the aptamer.

8. The lipid nanoparticle of claim 7, wherein the lipid nanoparticle is conjugated to a docking nucleic acid fragment comprising a nucleotide sequence complementary to the anchor nucleic acid fragment wherein the anchor nucleic acid fragment forms base pairs with the docking nucleic acid fragment, thereby immobilizing the aptamer on the lipid nanoparticle.

9. The lipid nanoparticle of claim 8, wherein the lipid nanoparticle further comprises a PEGylated lipid, wherein the docking a nucleic acid fragment is attached to the lipid nanoparticle via the polyethylene glycol (PEG) moiety of the PEGylated lipid.

10. The lipid nanoparticle of claim 9, wherein the pegylated lipid is 1,2-Distearoyl-sn-glycero-3-phosphorylethanolamine (DSPE).

11. The lipid nanoparticle of claim 1, wherein the heart injury is ischemia reperfusion injury.

12. The lipid nanoparticle of claim 1, wherein the agent is a HIF-1 α prolyl hydroxylase-2 (PHD2) inhibitor.

13. The lipid nanoparticle of claim 12, wherein the PHD2 inhibitor is IOX2, MK-8617, 2-methoxyestradiol, AKB-4924, IOX3 (FG-2216), FG-4497, roxadustat (FG-4592) Vadadustat (AKB-6548), Daprodustat (GSK1278863), Desidustat (ZYAN-1), Molidustat (Bay 85-3934) IOX4, Enarodustat (JTZ-951)), or a combination thereof.

14. The lipid nanoparticle of claim 1, wherein the agent is the agent capable of diagnosing the heart injury.

15. A pharmaceutical composition, comprising the lipid nanoparticle of claim 1 and a pharmaceutically acceptable carrier.

16. A method for delivering a therapeutic or diagnostic agent to an injured heart site, the method comprising administering to a subject in need thereof an effective amount of the pharmaceutical composition of claim 15.

17. The method of claim 16, wherein the subject is a human patient having or at risk for developing heart ischemia reperfusion injury.

* * * * *